United States Patent
Konofagou et al.

(10) Patent No.: US 11,013,938 B2
(45) Date of Patent: *May 25, 2021

(54) METHODS AND SYSTEMS FOR PERIPHERAL NERVE MODULATION USING NON ABLATIVE FOCUSED ULTRASOUND WITH ELECTROMYOGRAPHY (EMG) MONITORING

(71) Applicant: THE TRUSTEES OF COLUMBIA UNIVERSITY IN THE CITY OF NEW YORK, New York, NY (US)

(72) Inventors: Elisa E. Konofagou, New York, NY (US); Matthew Downs, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 311 days.

This patent is subject to a terminal disclaimer.

(21) Appl. No.: 15/661,909

(22) Filed: Jul. 27, 2017

(65) Prior Publication Data

US 2018/0028841 A1 Feb. 1, 2018

Related U.S. Application Data

(60) Provisional application No. 62/367,551, filed on Jul. 27, 2016, provisional application No. 62/485,661, filed on Apr. 14, 2017.

(51) Int. Cl.
*A61N 7/00* (2006.01)
*A61N 7/02* (2006.01)
(Continued)

(52) U.S. Cl.
CPC ............ *A61N 7/00* (2013.01); *A61B 5/389* (2021.01); *A61B 8/085* (2013.01); *A61N 7/02* (2013.01);
(Continued)

(58) Field of Classification Search
CPC .... A61N 7/00; A61N 7/02; A61N 2007/0052; A61N 2007/0021; A61B 5/0488;
(Continued)

(56) References Cited

U.S. PATENT DOCUMENTS 7,699,768 B2 4/2010 Kishawi et al.
8,206,299 B2 6/2012 Foley et al.
(Continued)

FOREIGN PATENT DOCUMENTS

EP 3 005 944 A1 4/2016
WO WO 2014/127091 A1 8/2014
WO WO 2014/160964 A1 10/2014

OTHER PUBLICATIONS

Colucci V, Strichartz G, Jolesz F, Vykhodtseva N, Hynynen K. Focused ultrasound effects on nerve action potential in vitro. Ultrasound Med Biol. 2009;35(10): 1737-1747. doi:10.1016/j.ultrasmedbio.2009.05.002 (Year: 2009).*

(Continued)

*Primary Examiner* — Serkan Akar
*Assistant Examiner* — Aminah Asghar
(74) *Attorney, Agent, or Firm* — Baker Botts, L.L.P.

(57) ABSTRACT

Techniques for modulating peripheral nerves using focused ultrasound (FUS) are provided. Methods include locating a peripheral nerve in a subject using an imaging probe, providing a FUS having one or more ultrasound parameters to a location on the peripheral nerve, and modulating the peripheral nerve. The methods can further include eliciting and measuring a physiological response from the FUS modulation, generating tissue deformation in the vicinity of the FUS modulation, and imaging the nerve and the tissue deformation simultaneously with FUS modulation. Systems for use in the modulation of peripheral nerves are also provided.

21 Claims, 23 Drawing Sheets

(51) Int. Cl.
  *A61B 5/389* (2021.01)
  *A61B 8/08* (2006.01)
  *A61B 5/00* (2006.01)
  *A61B 17/00* (2006.01)
  *A61B 90/00* (2016.01)

(52) U.S. Cl.
  CPC .............. *A61B 5/486* (2013.01); *A61B 5/4836* (2013.01); *A61B 2017/00039* (2013.01); *A61B 2017/00092* (2013.01); *A61B 2017/00154* (2013.01); *A61B 2017/00194* (2013.01); *A61B 2090/378* (2016.02); *A61N 2007/0021* (2013.01); *A61N 2007/0052* (2013.01)

(58) Field of Classification Search
  CPC ....... A61B 8/085; A61B 5/4836; A61B 5/486; A61B 2017/00039; A61B 2017/00154; A61B 2017/00194; A61B 2090/378; A61B 2017/00092
  See application file for complete search history.

(56) References Cited

U.S. PATENT DOCUMENTS

| | | | |
|---|---|---|---|
| 2007/0088345 A1 | 4/2007 | Larson et al. | |
| 2009/0005711 A1 | 1/2009 | Konofagou et al. | |
| 2009/0112133 A1 | 4/2009 | Deisseroth et al. | |
| 2010/0036292 A1* | 2/2010 | Darlington | A61N 7/00 601/2 |
| 2010/0087728 A1 | 4/2010 | Jarvik et al. | |
| 2010/0234728 A1 | 9/2010 | Foley et al. | |
| 2010/0318002 A1 | 12/2010 | Prus et al. | |
| 2011/0092781 A1* | 4/2011 | Gertner | A61B 5/4035 600/301 |
| 2011/0112394 A1 | 5/2011 | Mishelevich | |
| 2012/0065479 A1 | 3/2012 | Lahiji et al. | |
| 2012/0197163 A1 | 8/2012 | Mishelevich | |
| 2012/0289869 A1 | 11/2012 | Tyler | |
| 2013/0046229 A1 | 2/2013 | Konofagou et al. | |
| 2013/0079621 A1* | 3/2013 | Shoham | A61N 7/00 600/407 |
| 2013/0245486 A1 | 9/2013 | Simon et al. | |
| 2013/0245505 A1 | 9/2013 | Khuri-Yakub et al. | |
| 2013/0331905 A1 | 12/2013 | Haessler | |
| 2014/0094682 A1 | 4/2014 | Foley et al. | |
| 2014/0264660 A1 | 9/2014 | Rothberg et al. | |
| 2015/0065871 A1 | 3/2015 | Konofagou et al. | |
| 2015/0119763 A1 | 4/2015 | Canney et al. | |
| 2016/0059044 A1 | 3/2016 | Gertner et al. | |
| 2019/0069949 A1* | 3/2019 | Vrba | A61M 25/0147 |

OTHER PUBLICATIONS

U.S. Appl. No. 15/040,926 (US 2016/0242648), filed Feb. 10, 2016 (Aug. 25, 2016).
U.S. Appl. No. 15/040,926, Sep. 7, 2017 Non-Final Office Action.
International Search Report dated Sep. 9, 2016 in International Application No. PCT/US2016/040776.
International Search Report dated Sep. 27, 2017 in International Application No. PCT/US2017/044200.
U.S. Appl. No. 16/265,827, filed Feb. 1, 2019.
U.S. Appl. No. 15/040,926, Jun. 13, 2018 Notice of Allowance.
U.S. Appl. No. 15/040,926, Mar. 7, 2018 Response to Non-Final Office Action.
U.S. Appl. No. 16/265,827, May 14, 2020 Non-Final Office Action.
U.S. Appl. No. 16/265,827, Oct. 29, 2020 Final Office Action.
U.S. Appl. No. 16/265,827, Sep. 18, 2020 Response to Non-Final Office Action.
U.S. Appl. No. 16/265,827, Sep. 15, 2020 Applicant Initiated Interview Summary.
U.S. Appl. No. 16/265,827, Jan. 13, 2020 Response to Non-Final Office Action.
U.S. Appl. No. 16/265,827, Jul. 11, 2019 Non-Final Office Action.
Extended European Search Report dated Feb. 18, 2020 in Application No. EP 17835278.

* cited by examiner

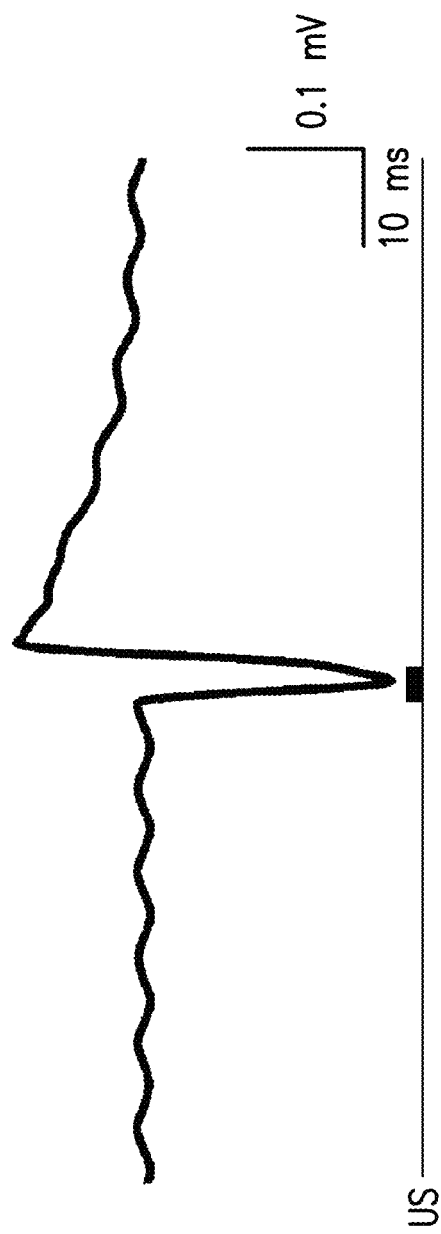
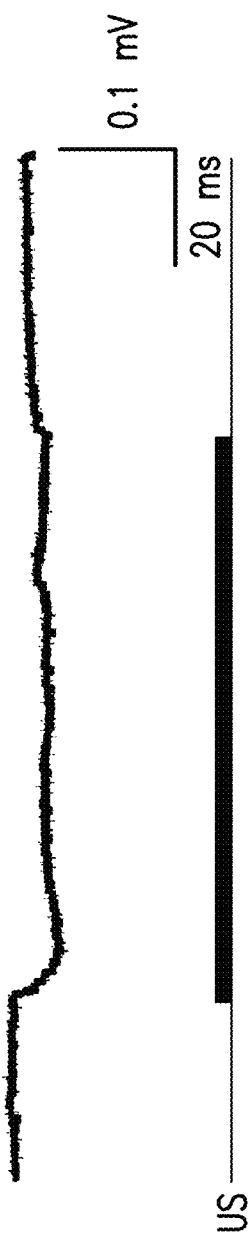
FIG. 2A
FIG. 2B

| Stimulation Parameters | | | | | |
|---|---|---|---|---|---|
| Peak Positive Pressure | Peak Negative Pressure | Focus (lateral x axial) | Intensity | Frequency | Pulse Duration | Duty Cycle |
| 5 MHz | 2-4 kHz | 0.45 x 3 mm | | 3.1 MHz | 0.58-1 ms | Continuous |

| Imaging Parameters | | | |
|---|---|---|---|
| Frequency | Pulse Repetition Frequency | Bandwidth | Transmit |
| 5 MHz | 2-4 kHz | 3-7 MHz | Plane Wave |

METHODS AND SYSTEMS FOR PERIPHERAL NERVE MODULATION USING NON ABLATIVE FOCUSED ULTRASOUND WITH ELECTROMYOGRAPHY (EMG) MONITORING

CROSS-REFERENCE TO RELATED APPLICATIONS

This application claims priority to U.S. Provisional Application Ser. No. 62/367,551, filed Jul. 27, 2016 and U.S. Provisional Application Ser. No. 62/485,661, filed Apr. 14, 2017, the contents of each of which are hereby incorporated by reference in their entirety.

STATEMENT REGARDING FEDERALLY-SPONSORED RESEARCH

This invention was made with government support under grants EB009041 and AG038961 awarded by the National Institutes of Health and by HR0011-15-2-0054 awarded by DOD/DARPA. The government has certain rights in the invention.

BACKGROUND

Ultrasound is a versatile technology that is used in many different fields such as imaging, chemical processes, and therapeutics. Ultrasound imaging is a widespread technique for monitoring fetal development or cardiac abnormalities, and can be employed as a therapeutic treatment for procedures that require non-invasive, target specific, and temporally efficient procedures. These techniques can utilize the ability of the ultrasound to have thermal, mechanical or a combined thermal/mechanical effect. For example, focused ultrasound (FUS) can involve concentrating multiple intersecting beams of ultrasound on a target region using an acoustic lens. Given the high precision and non-invasive nature of the technique, FUS-related methods have been utilized for the treatment of a variety of diseases including prostate cancer and uterine fibroids.

A subset of therapeutic ultrasound utilizing FUS can be effective at stimulating, or inhibiting neuronal activity in both the central nervous system (CNS) and peripheral nervous system (PNS). For example, FUS can be effective to open the blood-brain barrier and thus can facilitate the diffusion of drug molecules into brain tissue. Moreover, FUS can modulate neuronal activity by stimulating specific regions in the CNS and FUS can stimulate or inhibit the PNS due to either thermal or mechanical effects of FUS. For example, thermal effects can be responsible for blocking action potentials by increasing the temperature of the solution surrounding the ex vivo nerve, first reducing the peak-to-peak response, and eventually blocking the action potential from propagating throughout the axon. A mechanical effect can be indicated during FUS stimulation, for example, the activation of mechanosensitive ion channels with specific FUS parameters during in vitro stimulation of the *xenopus* oocyte system. FUS stimulation targeting the axon of the sciatic nerve can also elicit compound action potentials ex vivo.

Certain structures in the CNS can be targeted to examine physiological effects of FUS stimulation. Stimulating specific brain regions can result in the delay of antisaccade motion in monkeys and limb twitching in mice, to enhanced tactile discrimination and generation of phosphenes in humans. This illustrates that FUS can have an excitatory or inhibitory effect on neurons, with different potential mechanisms of action depending on the ultrasound parameters employed.

Further, certain methods that treat peripheral nervous system (PNS) diseases, such as drug therapy, electrical stimulation and surgical interventions, can have certain disadvantages. For example, drug therapy can be considered non-specific and spatially untargeted. Electrical stimulation can be either invasive and target the specific damaged peripheral nerve, or non-invasive and non-specific, targeting the region around the damaged peripheral nerve. Therapeutic ultrasound can provide a non-invasive, and targeted approach for treating peripheral nerves, eliminating the potential side effects of drug therapies and invasive surgery. Additionally, FUS systems can be relatively inexpensive and portable, allowing clinicians to treat a larger patient population.

Accordingly, there remains a need in the art for improved techniques for targeted, specific, and non-invasive treatment options that can modulate peripheral nerves, for example, for the treatment of PNS diseases.

SUMMARY OF THE INVENTION

The presently disclosed subject matter provides techniques for modulating peripheral nerves in a subject using focused ultrasound (FUS).

In certain aspects, methods for modulating a peripheral nerve in a subject using a FUS assembly having one or more ultrasound parameters are provided. Methods can include adjusting the one or more ultrasound parameters to adapt a FUS for a location on the peripheral nerve, and modulating the peripheral nerve with the FUS. In certain embodiments, the methods can further include locating the peripheral nerve using an imaging probe prior to adjusting the one or more ultrasound parameters. As embodied herein, example methods can include modulating a sciatic nerve, a tibial nerve, or a sacral nerve.

As embodied herein, and without limitation, the imaging probe can be a B-mode imaging probe. The ultrasound source can include a high intensity focused ultrasound (HIFU) transducer with a 3.57 MHz center frequency, a 0.46×3.55 mm focal area and a 35 mm focal depth, a 20 MHz function waveform generator, and a 150 W amplifier. The one or more ultrasound parameters can include at least one of a peak negative pressure, a stimulation duration, a duty cycle, and a pulse repetition frequency (PRF). For example, and as embodied herein, the peak negative pressure can be from about 1.1 MPa to about 8.8 MPa. The stimulation duration can be from about 0.8 ms to about 1 s. The duty cycle can be from about 15% to about 100%. The PRF can be from about 1 kHz to about 50 kHz. As embodied herein, the peak negative pressure can be from about 3.2 MPa to about 5.7 MPa, the stimulation duration can be from about 0.8 ms to about 10.5 ms, the duty cycle can be from about 35% to about 100%, and the PRF can be from about 1 kHz to about 50 kHz.

As embodied herein, example methods can include eliciting and measuring a physiological response during or after FUS modulation. As embodied herein, and without limitation, the measuring physiological response can include acquiring EMG signals from a muscle tissue. In certain embodiments, the method can include modulating one or more ultrasound parameters to change timing of the physiological response.

As embodied herein, the method can further include causing tissue deformation in the vicinity of FUS modulation with an acoustic radiation force generated by the FUS. The tissue deformation can range from about 8.5 µm to about 422 µm. In certain embodiments, the tissue deformation can facilitate action potential firing within the nerve and elicit an EMG activity.

As embodied herein, the method can further include imaging the nerve and the tissue deformation simultaneously with FUS modulation. In certain aspects, the method can further include monitoring a thermal effect elicited by the FUS modulation.

The presently disclosed subject matter also provides systems for modulating a peripheral nerve in a subject using FUS. As embodied herein, an example system can include an imaging probe for locating the peripheral nerve, an ultrasound assembly, including a high intensity focused ultrasound (HIFU) transducer, a function generator, and an amplifier, for providing a FUS having one or more ultrasound parameters to a location on the peripheral nerve, and a processor, coupled to the ultrasound assembly, for adjusting the one or more ultrasound parameters to adapt the FUS for a location on the peripheral nerve.

As embodied herein, the system can further include a mechanical positioning system for placing the ultrasound assembly and the imaging probe. In certain embodiments, the system can include an imaging system, operatively coupled to the processor, for imaging the peripheral nerve and/or surrounding tissue during FUS modulation. In certain embodiments, the imaging system can be a pulse-echo image transducer. As embodied herein, and without limitation, the system can be a transdermal patch.

BRIEF DESCRIPTION OF THE DRAWINGS

FIGS. 2A and 2B are graphs demonstrating artifacts from EMF noise according to Example 1 of the present disclosure.

FIG. 3A is a graph showing a single spike EMG response to FUS stimulation of the long duration group (1-10 ms stimulation duration). FIG. 3B is a graph showing a double spike EMG response to FUS stimulation of the long duration group. FIG. 3C is a graph showing two EMG spikes for the short FUS stimulation duration group (0.8 ms stimulation duration).

FIG. 7A is a graph depicting the average delay from onset of stimulation to EMG signal and standard deviation for each pressure and duty cycle. FIG. 7B is a graph showing the average peak-to-peak and standard deviation EMG for each pressure and duty cycle.

FIG. 9A is a an image showing the sciatic nerve bundle and surrounding neural and muscle tissue for the FUS stimulated group with parameters found for successful EMG and muscle activation. FIG. 9B is an image of the positive control group showing damaged areas by applying FUS stimulation for 0.5 s. FIG. 9C is a graph showing plot of pressure vs average ±s.d. temperature increase in an ex vivo mouse hind limb from baseline.

FIG. 9C also includes a raster plot of temperature increase in an ex vivo mouse hind limb during FUS stimulation at a PNP of 4.5 MPa.

FIG. 19A is a graph showing no ultraharmonics or broadband emissions. FIGS. 19B and 19C are graphs showing ultraharmonics without broadband emissions. FIG. 19D is a graph showing ultraharmonics and broadband emissions.

DETAILED DESCRIPTION

Figure 1:
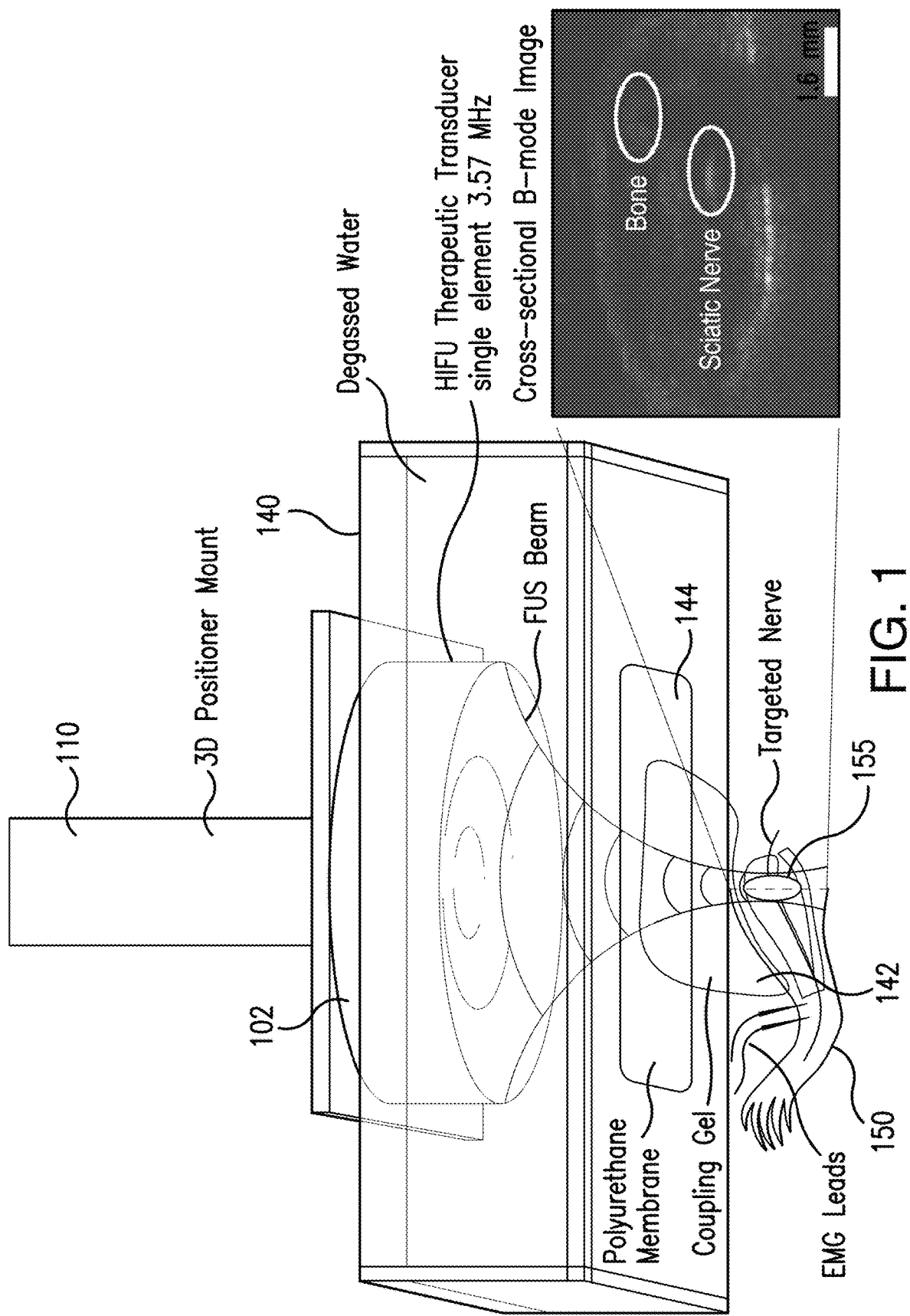
FIG. 1 is a diagram illustrating an exemplary embodiment of a system for modulating peripheral nerves in a subject using an ultrasound assembly according to the disclosed subject matter.

The presently disclosed subject matter provides techniques for modulating nerves using focused ultrasound (FUS). According to one aspect of the disclosed subject matter, methods and systems for applying FUS to the peripheral nerves of a subject are provided. It was found that FUS is effective at stimulating peripheral nerves and eliciting a physiological response in vivo. Furthermore, the physiological response generated by FUS was comparable to that generated by conventional electrical stimulation methods.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the presently disclosed subject matter. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of", and "consisting essentially of," the embodiments or elements presented herein, whether explicitly set forth or not.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, "treatment" or "treating" refers to inhibiting the progression of a disease or disorder, or delaying the onset of a disease or disorder, whether physically, e.g., stabilization of a discernible symptom, physiologically, e.g., stabilization of a physical parameter, or both. As used herein, the terms "treatment," "treating," and the like, refer to obtaining a desired pharmacologic and/or physiologic effect. The effect can be prophylactic in terms of completely or partially preventing a disease or condition, or a symptom thereof and/or can be therapeutic in terms of a partial or complete cure for a disease or disorder and/or adverse effect attributable to the disease or disorder. "Treatment," as used herein, covers any treatment of a disease or disorder in an animal or mammal, such as a human, and includes: decreasing the risk of death due to the disease; preventing the disease of disorder from occurring in a subject which can be predisposed to the disease but has not yet been diagnosed as having it; inhibiting the disease or disorder, i.e., arresting its development (e.g., reducing the rate of disease progression); and relieving the disease, i.e., causing regression of the disease.

As used herein, the term "subject" includes any human or nonhuman animal. The term "nonhuman animal" includes, but is not limited to, all vertebrates, e.g., mammals and non-mammals, such as nonhuman primates, dogs, cats, sheep, horses, cows, chickens, amphibians, reptiles, etc. In certain embodiments, the subject is a pediatric patient. In certain embodiments, the subject is an adult patient.

As used herein, an "effective amount" refers to an amount of the compound sufficient to treat, prevent, manage the disease, or to generate a physiological response. An effective amount can refer to the amount of a compound that provides a beneficial physiological response in the treatment or management of the disease, and as such, an "effective amount" depends upon the context in which it is being applied. In the context of administering anesthetics during FUS modulation in a subject, an effective amount of anesthetics described herein is an amount sufficient to elicit an anesthetizing effect in the subject. An effective amount can be administered in one or more administrations. Further, a therapeutically effective amount can mean the amount of therapeutic alone, or in combination with other therapies, that provides a therapeutic benefit in the treatment or management of the disease, which can include a decrease in severity of disease symptoms, an increase in frequency and duration of disease symptom-free periods, or a prevention of impairment or disability due to the disease affliction. The term can encompass an amount that improves overall therapy, reduces or avoids unwanted effects, or enhances the therapeutic efficacy of or synergies with another therapeutic agent.

For the purpose of illustration, FIG. 1 is a diagram depicting an exemplary system for peripheral nerve modulation according to the disclosed subject matter. Systems according to the disclosed subject matter can include various combinations of some or all of the components of FIG. 1 according to the desired application(s) and are not limited to the particular combinations of components described herein.

For purpose of illustration and not limitation, the system can include an ultrasound assembly 102 for providing FUS having one or more ultrasound parameters to a location on the peripheral nerve. The ultrasound assembly can include a FUS transducer, a function generator, and an amplifier. As embodied herein, the FUS transducer can be a high intensity focused ultrasound (HIFU) transducer with a 3.57 MHz center frequency, a 0.46×3.55 mm focal area and a 35 mm focal depth (SU-107, SonicConcepts, Seattle, Wash., USA). The transducer can be driven by any suitable equipment, such as a function generator. For example, and as embodied herein, the function generator can be a 20 MHz function waveform generator (33220A, Keysight Technologies Inc., Santa Rosa, Calif., USA). The function generator can be joined to an amplifier. As embodied herein, the amplifier can be a 150 W amplifier (A150, Electronics & Innovation, Ltd. Rochester, N.Y., USA). The amplifier can increase the power from the generator, e.g., by about 20 dB to about 100 dB. A signal from the function generator can be amplified by the amplifier, and the transducer can convert the amplified signal into FUS.

As embodied herein, the system can further include an imaging probe for locating the peripheral nerve. The imaging probe can be a B-mode imaging probe. For example, and as embodied herein, the imaging probe can be a L22-14V imaging probe with 128 elements, linear array and 18.5 MHz (Verasonics, Kirkland, Wash., USA).

In certain embodiments, the system can further include a processor, coupled to the ultrasound assembly, for adjusting one or more ultrasound parameters to adapt the FUS for a location on the peripheral nerve. For example, the processor can be configured to perform the instructions specified by software stored in a hard drive, a removable storage medium, or any other storage media. The software can include computer codes, which can be written in a variety of languages, e.g., MATLAB and/or Microsoft Visual C++. Additionally or alternatively, the processor can include hardware logic, such as logic implemented in an application-specific integrated circuit (ASIC). The processor can be configured to control one or more of the system components described above. For example, and as embodied herein, the processor can be configured to control imaging and ultrasound stimulation. Additionally or alternatively, the processor can be configured to control the output of the function generator and/or the transducer to provide the FUS to the subject.

Referring to FIG. 1, the system can further include a mechanical positioning system 110 for placing the ultrasound assembly and the imaging probe. As embodied herein, the positioning system can be used to place both the ultrasound transducer and the imaging probe with submillimeter resolution. The positioning system can be a 3D positioner mount system (Velmex, Bloomfield, N.Y., USA), which can be used to align the FUS from the transducer with a target area on the subject. The 3D positioner mount system can move the transducer in the x-, y-, and z-directions. For example, the 3D positioner mount system can include a motor and a controller. In certain embodiments, the 3D positioner mount system can move the transducer, for example and without limitation, within a predefined grid. The size and resolution can be selected by the user. The 3D positioner mount system can move the transducer within the grid to produce a random raster sonication on the subject using the FUS.

As embodied herein, the system can have high target specificity, and can achieve a resolution in the submillimeter range. For example, and as embodied herein, the system can provide FUS to a target area that is from about 0.1 mm to about 5 mm, or from about 0.1 mm to about 1 mm, or from about 0.5 mm to about 5 mm, or from about 0.75 mm to about 2 mm. This high target specificity enables the FUS to target a specific region of the peripheral nerve.

In certain embodiments, the system can be a stationary device. In certain embodiments, the system can be a portable device. Additionally or alternatively, the system can be configured as a wearable device. As embodied herein, the ultrasound assembly can be a transdermal patch. For example, in certain embodiments, the system can be configured as a transdermal patch having an array of multiple transducers operating in unison. The stationary device can be used as an alternative to, or in combination with, the portable device, for example and without limitation, in the modulation of peripheral nerves.

Ultrasound can refer to a sound wave having a frequency above that of human hearing, e.g., greater than 16 kHz. In certain embodiments, the FUS can have a frequency greater than about 16 kHz. In certain embodiments, the FUS can have a frequency from about 50 kHz to about 20 MHz, or from about 0.1 MHz to about 5 MHz, or from about 0.5 MHz to about 3 MHz, or from about 1 MHz to about 2 MHz. In certain embodiments, the FUS can have a sweep of different frequencies. As embodied herein, the FUS can have a center frequency of about 3.57 MHz.

The FUS can be delivered in multiple different forms. For example, and not limitation, the FUS can be a chirp, i.e., a swept frequency cosine signal. The swept frequency cosine signal can be linear, quadratic, or logarithmic. In certain embodiments, noise can be reduced using a continuous ultrasound wave. Thus, in certain embodiments, the FUS can be a continuous ultrasound wave.

The FUS can have one of more ultrasound parameters. As embodied herein, the one or more ultrasound parameters can include at least one of a peak negative pressure, a stimulation duration, a duty cycle, and a pulse repetition frequency (PRF). The ultrasound parameters can be pre-programmed and/or adjusted. The peak negative pressure (input pressure) can be from about 1.1 MPa to about 8.8 MPa, or from about 3.2 MPa to about 5.7 MPa, or at least about 3.2 MPa for the frequency of 3.57 MHz. The stimulation duration can be from about 0.8 ms to about 1 s, or from about 0.8 ms to about 10.5 ms, or from about 1 ms to about 10 ms. The duty cycle can be from about 15% to about 100%, or from about 35% to about 100%, or at least about 35%. The PRF can be from about 1 kHz to about 50 kHz, or from about 1 kHz to about 25 kHz, or from about 1 kHz to about 10 kHz, or from about 1 kHz to about 5 kHz.

As embodied herein, the system can further include an imaging system, operatively coupled to the processor, for imaging the peripheral nerve and/or surrounding tissue during FUS modulation. For example, and as embodied herein, the imaging system can be a pulse-echo imaging transducer. The pulse-echo imaging transducer can function at 7.8 MHz and have 104 elements.

With further reference to FIG. 1, the system can further include a chamber 140 containing a couplant, such as oil or water, for transmitting the ultrasound. Additionally or alternatively, a conductive material 142 can be placed on the subject 150. For example, such conductive material includes ultrasound gel and/or water. The chamber 140 can include a membrane 144 located adjacent to the position of the subject 150, to facilitate the transmission of the ultrasound through the chamber.

Additional details of systems and techniques for using FUS can be found, for example and without limitation, in International Patent Application Serial No. PCT/US16/40776, which is incorporated by reference herein in its entirety.

As embodied herein, the peripheral nerves can include a sciatic nerve, a tibial nerve, or a sacral nerve. Additionally or alternatively, the peripheral nerves can include one or more of the following nerves: a vagus nerve, a intercostals nerve, a subcostal nerve, an iliohypogastric nerve, an ilioinguinal nerve, a lateral cutaneous of thigh nerve, a genitofemoral nerve, a musculocutaneous nerve, a radial nerve, a median nerve, an ulnar nerve, an obturator nerve, a femoral nerve, a muscular branches of femoral nerve, a saphenous nerve, a sciatic nerve, a tibial nerve, a sacral nerve, a common peroneal nerve, a deep peroneal nerve, a superficial peroneal nerve, sural nerve, a cranial nerve, a spinal cord, a spinal cord element, a spinal root, a dorsal root ganglion, a sympathetic chain ganglion, a brachial nerve, and/or a hair follicle.

The disclosed techniques can be used in a wide variety of clinical applications. For example, FUS can be used to treat various peripheral nervous system diseases, including but not limited to, acute or chronic neuropathic pain, Guillain-Barre syndrome, urinary or fecal incontinence, amyloid neuropathy, brachial plexus neuropathy, complex regional pain syndrome, diabetic neuropathy, mononeuropathy, nerve compression syndrome, neuralgia, neuritis, peripheral nervous system neoplasm, or polyneuropathy. Additionally or alternatively, FUS can be used to treat other diseases including epilepsy, depression, metabolic disorders, chronic trunk or limb pain, radicular pain, diabetic neuropathy, motor or sensory recovery, nerve or tissue repair or healing, vertigo, nystagmus, motion sickness, tinnitus, and/or hair regrowth.

In certain embodiments, it can be desirable for the subject to receive FUS treatment in a clinic. For example, certain conditions can be treated with a single treatment or infrequent, periodic treatments that can be performed by a clinician. In certain embodiments, it can be more convenient for the subject to receive FUS treatment outside a clinic. For example, certain conditions require frequent or regular treatments, and therefore it can be more desirable to perform the treatment in the subject's home. For example, a subject diagnosed with such a condition can be provided with a portable device that can be used to perform FUS treatments outside a clinical setting. FUS can be provided by the portable device when symptoms occur and/or pursuant to a predetermined schedule. The portable device, such as a transdermal patch, can be pre-programmed with particular ultrasound parameters. In certain aspects, an at-home transdermal electrical stimulation system can be used to perform FUS treatments. The system can be an all-in-one system for both targeting and stimulating the peripheral nerve. Such system can also include a multi-element array. Additionally and alternatively, the ultrasound parameters can be adjusted according to the symptoms experienced by the subject, the biomarkers experienced by the subject and/or picked up by biosensors on a device, and/or smart device questioning of the subject. The duty cycle can be tailored to the subject. Remote programming can also be performed by the physician based on data analytics.

The disclosed techniques can be applied to a variety of living subjects, including humans and animals. For example, and as embodied herein, the subject can be anesthetized using an effective amount of anesthetics. The anesthetics can be sodium pentobarbital, isoflurane, or ketamine. The anesthetics can be provided in a certain dosage relative to the body weight of the subject. For purpose of illustration and not limitation, sodium pentobarbital can be administered from about 25 mg/kg to about 100 mg/kg, or from about 50 mg/kg to about 75 mg/kg. Modulation of the peripheral nerves using FUS can be affected at least in part by the type of anesthesia used. Anesthesia can also help secure the subject in a fixed position relative to an ultrasound source. As embodied herein, the subject can be awake or asleep in a specific mode. For example, FUS can be delivered to the subject after sleep is behaviorally detected.

In certain aspects, the present disclosure provides methods for modulation of a peripheral nerve in a subject using a FUS assembly having one or more ultrasound parameters including locating the peripheral nerve using an imaging probe; adjusting the one or more ultrasound parameters to adapt a FUS for a location on the peripheral nerve; and modulating the peripheral nerve with the FUS. In certain aspects, modulating the peripheral nerve with FUS can be non-invasive and have minimal side effects. In certain aspects, modulating the peripheral nerve with FUS does not cause any damage to the nerve or surrounding tissues.

As embodied herein, the method of the present disclosure can further include eliciting a physiological response. In certain aspects, the physiological response can be observed during FUS modulation. In certain aspects, the physiological response can be observed after FUS modulation is ceased. In certain aspects, the physiological response can be observed both during and after FUS stimulation.

The physiological response can include any physical change as a result of peripheral nerve modulation. For example, the physiological response can include one or more of the following responses: muscle contraction, a body movement, an eye movement, and/or pupil dilation. As embodied herein, the physiological response can also include an electromyography (EMG) activity from a muscle tissue. The EMG activity can be detected using an electromyograph. In certain embodiments, EMG recording can be acquired using needle electrodes placed in a muscle tissue. As embodied herein, additional physiological responses including acceleration, EMG, temperature, heart rate, blood sugar level, moisture, and pressure can be detected by biosensors on a probe or a patch. For example and not limitation, such biosensors can include an accelerometer, EMG, thermometer, heart rate, glucose meters, moisture detectors, pressure gauges). Additionally or alternatively, smart apps programmed on the system or another device can be used to test or track eye movement, test cognition, mood, quality of life, and/or treatment scores.

As embodied herein, methods for modulation of a peripheral nerve in a subject using a FUS assembly can further include eliciting and measuring a physiological response during or after FUS modulation. In certain embodiments, the physiological response is measured by acquiring EMG signals from a muscle tissue. The muscle tissue can be adjacent to the modulated peripheral nerve. Additionally or alternatively, the muscle tissue can be remote from the modulated peripheral nerve. For example, and as embodied herein, the peripheral nerve can be a sciatic nerve and the muscle tissue can be a tibialis anterior muscle. The peripheral nerve can be a tibial nerve and the muscle can be a foot or a calf muscle. The peripheral nerve can be a sacral nerve and the muscle can be a rectal or a bladder muscle. In certain embodiments, the methods can further include recording muscle activation along with EMG activity using a video recording device.

As embodied herein, the method of the present disclosure can further include modulating one or more ultrasound parameters to change the timing of the physiological response. For purpose of illustration and not limitation, the ultrasound parameters can be changed such that an EMG activity is only detected after FUS stimulation has ceased as opposed to during FUS stimulation. The ultrasound parameters that can be changed include peak negative pressure, stimulation duration, duty cycle, and/or pulse repetition frequency (PRF).

As embodied herein, the methods of the present disclosure can further include generating a certain acoustic radiation force onto the nerve and/or surrounding tissue with FUS. An increased acoustic radiation force can increase the ability of the FUS to elicit a physiological response in a subject. In certain aspects, the acoustic radiation force can be calibrated to achieve the desired response without compromising safety. In certain aspects, the acoustic radiation force can be greater than or equal to a threshold acoustic pressure to evoke the physiological response. For purpose of illustration and not limitation, the acoustic radiation force can range from about 0.5 nanonewtons to about 5.4 meganewtons.

As discussed above, FUS can generate a certain acoustic radiation force onto the nerve and/or surrounding tissue in the subject. Thus, in certain aspects, the method of present disclosure can further include measuring the acoustic radiation force. For example, and as embodied herein, the acoustic radiation force can be measured using a force balance. Measuring acoustic radiation force can allow FUS parameters to be properly adjusted and/or calibrated to avoid damaging effects. In certain aspects, measured acoustic radiation force can be converted to determine the tissue deformation at the focal region.

As embodied herein, the acoustic radiation force generated by the FUS can cause tissue deformation in the vicinity of FUS modulation. The tissue deformation can be approximated based on the input voltages and pressures, e.g., based on the Young's modulus of the tissue as detailed in Example 1. For example, and as embodied herein, the tissue deformation can range from about 8.5 µm to about 422.8 µm, or from about 14 µm to about 422 µm. The input voltage can range from about 0.1 V to about 0.9 V. Additionally or alternatively, the tissue deformation can be monitored and/or measured in real-time. In certain embodiments, real-time monitoring of tissue deformation can be used to provide image-guided treatment via FUS. Thus, as embodied herein, the method of the present disclosure can further include imaging the nerve and the tissue deformation simultaneously with FUS modulation of peripheral nerves. Such method can allow the mechanisms of FUS on the peripheral nervous system to be dissected and controlled. The imaging can be performed with a transducer that is designed to incorporate both the FUS transducer and an imaging transducer. Such transducer can simultaneously image the mechanical perturbation of the tissue during FUS modulation in vivo. For example, and as embodied herein, the imaging transducer can be a pulse-echo imaging transducer. The pulse-echo imaging transducer can be a 104-element, 7.8-MHz, pulse-echo imaging transducer.

In certain embodiments, the tissue deformation generated is large enough to facilitate action potential firing within the nerve. In certain aspects, the action potential firing can further elicit a physiological response such as an EMG activity. In certain aspects, the mechanical forces from the FUS can be converted into an electrical signal by forcing open the voltage gated ion channels in the nodes of Ranvier. In certain embodiments, tissue deformation can itself be therapeutic. For example and not limitation, targeted deep massage of micro muscles and/or nerve sites can be performed in certain embodiments.

As embodied herein, the method of the present disclosure can further include monitoring a thermal effect elicited by the FUS modulation. For example, the thermal effect can be monitored by embedding wire thermocouples in the muscle tissue adjacent to the stimulated peripheral nerve. Such thermal monitoring can help determine whether the FUS stimulation effects are due to temperature increase or due to mechanical effects.

In certain aspects, the present disclosure provides methods for treating peripheral nervous system disease in a subject including modulating one or more peripheral nerves in the subject with a FUS. For purpose of illustration and not limitation, the subject can have one or more of the following diseases: acute or chronic neuropathic pain, Guillain-Barre syndrome, urinary or fecal incontinence, amyloid neuropathy, brachial plexus neuropathy, complex regional pain syndrome, diabetic neuropathy, mononeuropathy, nerve compression syndrome, neuralgia, neuritis, peripheral nervous system neoplasm, polyneuropathy migraine, or headache.

The systems and techniques of the disclosed subject matter provide advantages over certain existing therapies for peripheral nervous system diseases. For purpose of illustration and not limitation, advantages of the systems of techniques described herein include non-invasive procedures, high target specificity, minimal side effects, low cost, and increased portability. Additionally, the systems and techniques described herein can provide non-invasive treatment options for other medical conditions including epilepsy, depression, metabolic disorders, chronic trunk or limb pain, radicular pain, diabetic neuropathy, motor or sensory recovery, nerve or tissue repair or healing, vertigo, nystagmus, motion sickness, tinnitus, and/or hair regrowth.

The systems and techniques of the disclosed subject matter can further be extended to stimulate peripheral fields. For example, the FUS can stimulate or modulate general transdermal fields of neural elements or nerve plexuses instead of or in addition to a peripheral nerve. Additionally, the system and techniques described herein can be applied to stimulate visceral or smooth muscles to modulate the function of other organs or structures, such as bladder, kidney, spleen, sex organ, transcranial brain, and/or cortical and deep structures.

EXAMPLES

The present disclosure is further illustrated by the following Examples which should not be construed as further limiting.

Example 1: Non-Invasive Peripheral Nerve Stimulation Via Focused Ultrasound In Vivo This Example provides methods and systems for non-invasive peripheral nerve stimulation via focused ultrasound in vivo. Focused ultrasound (FUS) has been employed on a wide range of clinical applications to safely and non-invasively achieve desired effects that have previously required invasive and lengthy procedures with conventional methods. Conventional electrical neuromodulation therapies that are applied to the peripheral nervous system (PNS) are invasive and/or non-specific. Recently, focused ultrasound has demonstrated the ability to modulate the central nervous system and ex vivo peripheral neurons. Here, non-invasive stimulation of the sciatic nerve eliciting a physiological response in vivo is demonstrated with FUS. FUS was applied on the sciatic nerve in mice with simultaneous electromyography (EMG) on the tibialis anterior muscle. EMG signals were detected during or directly after ultrasound stimulation along with observable muscle contraction of the hind limb. Transecting the sciatic nerve downstream of FUS stimulation eliminated EMG activity during FUS stimulation. Peak-to-peak EMG response amplitudes and latency were found to be comparable to conventional electrical stimulation methods. Histology along with behavioral and thermal testing did not indicate damage to the nerve or surrounding regions. The findings presented herein demonstrate that FUS can serve as a targeted, safe and non-invasive alternative to conventional peripheral nervous system stimulation to treat peripheral neuropathic diseases in the clinic.

In this Example, it is demonstrated for the first time that FUS stimulation of peripheral nerves in vivo can elicit a physiological response. The sciatic nerve in anesthetized mice was stimulated via FUS while EMG signals were recorded through needle electrodes placed into the tibialis anterior muscle. Successful stimulation of the sciatic nerve rather than the surrounding muscle tissue was verified through transecting the nerve downstream of the FUS targeted region, which completely eliminated the electromyography (EMG) signal. These findings indicate that FUS can be used for the excitation of peripheral nerves, non-invasively and safely resulting in the desired physiological response.

Methods

All procedures with mice were approved by the Institutional Animal Care and Use Committee of Columbia University and ACURO. Male C57BL/6J mice weighing between 22-28 g were used in all experiments (n=42). Mice were housed in rooms with 12-hour light/dark cycles and provided food and water ad lib. Mice were anesthetized with 50 mg/kg pentobarbital for all FUS and electrical stimulation experiments. A heating pad was used to maintain proper body temperature throughout the experiments. For non-survival studies (histology, electrical stimulation, thermocouple) mice were sacrificed by cervical dislocation before harvesting the hind limbs.

All FUS experiments were conducted with a HIFU transducer with a 3.57 MHz center frequency (0.46×3.55 mm focal area, 35 mm focal depth; SU-107, SonicConcepts, Seattle, Wash., USA). The driving signal was derived from a function generator (33220A, Keysight Technologies Inc., Santa Rosa, Calif., USA) and amplified through a 150 W amplifier (A150, Electronics & Innovation, Ltd. Rochester, N.Y., USA). The sciatic nerve was targeted as it innervates the leg muscles branching into the peroneal and tibial nerves. FUS parameters employed during the experiments ranged from 1.1-8.3 MPa peak negative pressure, 4 ms-1 s stimulation duration, 15-100% duty cycle, 1 kHz PRF. Accounting for the pressure attenuation through the muscle to reach the sciatic nerve, delivered pressures ranged from 0.7-5.4 MPa. Changes for each parameter were modified as such: Duty cycle 15, 35, 50, 90, 100%, Pressure 0.6 MPa increments and duration 100 ms increments, unless under 10 ms, then by 1 ms increments. Each combination of parameter was tried n=5 times for a total of 2,000 trials. The sciatic nerve was targeted for FUS experiments through b-mode imaging with a L22-14V imaging probe (128 elements, linear array, 18.5 MHz, Verasonics, Kirkland, Wash., USA). Coupling gel was used for both b-mode imaging and FUS stimulation. A focusing cone filled with degassed water was used with the FUS stimulation. A mechanical positioning system was utilized for placement of both B-mode and stimulating transducers with submillimeter resolution (Velmex, Bloomfield, N.Y., USA). Stimulation and imaging were controlled and recorded through in-house developed Matlab code (Mathworks, Natick, Mass., USA). EMG recordings were acquired with two stainless steel needle electrodes placed in the Tibialis Anterior muscle and recorded at 5 MHz (Biopac, Goleta, Calif., USA). A radiation force balance was used to determine radiation force generated by the transducer. Video recordings were acquired simultaneously with stimulation to archive muscle activation along with EMG activity.

Electrical stimulation experiments (n=9) were conducted with a S48 single channel stimulator (Grass, Warwick, R.I., USA). A small incision was made through the skin and thigh muscle then the sciatic nerve was teased apart from the surrounding connective tissue and muscle. Platinum electrodes were coiled around the sciatic nerve. The following parameters were explored: 1-10 V, 1-10 mA, 200-500 µs with 1 V, 1 mA and 50 µs step sizes based on parameters employed in prior electrical stimulation studies treating peripheral neuropathy. EMG recordings were the same as outlined above. Between stimulations 0.9% saline solution was used to hydrate the nerve and exposed tissue.

Histology samples of both hind limbs were collected (n=8 FUS stimulation, n=8 negative control, n=1 positive control), fixed in 0.4% PFA, 70% EtOH rinse and embedded in paraffin. Stimulation parameters were as follows: 4.5 MPa, 90% DC, 1 kHz PRF, 4.5-9 ms stimulation duration. Samples were sectioned coronally acquiring 5 µm slices with 200 µm interstice gaps and affixed to slides. Samples were stained with H&E. A blinded study was then conducted to determine damage to the tissue as follows: inflammation/abnormal cell morphology, red blood cell extravasation, and cell membrane rupture.

Open field tests were conducted in a 30 cm³ opaque white box (n=4 FUS stimulation, n=4 control). FUS stimulation parameters were as follows: 4.5 MPa, 90% DC, 1 kHz PRF, 4.5-9 ms stimulation duration. Only one of the hind limbs was stimulated 20 times and verified with video recording, as EMG electrodes can introduce damage to the limbs and generate false positives. Behavioral testing was recorded on days −1, 1, 2, and 3 with day 0 being the day FUS stimulation was applied. Behavioral testing was recorded and analyzed using the EthoVision behavioral analysis suite (Noldus, Wageningen, The Netherlands). The behavioral characteristics analyzed were the total distance traveled, number of rotations to ipsilateral side of FUS stimulation, and time spent in center versus along the walls of the cube (Center=15×15 cm square in middle of cube, along walls=remaining area between center square and walls).

Thermocouple experiments were conducted with the FUS transducer and parameters as follows: 0.7-5.4 MPa peak negative pressure, 5 ms stimulation duration, 100% duty cycle, 1 kHz PRF. Wire thermocouples (Omega, Norwalk, Conn., USA) were embedded in ex vivo hind limb tissue along the sciatic nerve. Raster scans of a 5 mm² area were acquired with 0.5 mm step sizes (n=5) with a temperature sampling rate of 20 Hz. Samples were kept at an average 21° C. throughout experiments.

Radiation force experiments utilized a radiation force balance to measure the acoustic power of the transducer. A brush absorber was placed in a tank and filled with DI water before degassing the entire setup. Once degassed, this tank was placed on a weight balance and set to zero. The transducer was positioned above the brush absorber with the focal area targeting within the brush. Voltages ranging from 0.1-0.9 V were applied three times to find an average increased weight (g) displayed from the radiation force exerted on the weight balance. To determine the acoustic power from the measurements the following equation (1) was used:

$$\text{Acoustic Power} = \frac{2Mgc}{\left(1 + \cos\left(\arcsin\left(\frac{a}{F}\right)\right)\right)} \times e^{2\alpha d} \qquad (1)$$

where M is the mass reading from the weight balance, g is gravity, c is speed of sound in water at room temperature, a is half the length of the transducer aperture, F is the focal length, a is the acoustic attenuation of water and d is the distance of the transducer the acoustic absorber. With this acoustic power, it is possible to find the radiation force according to equation (2):

$$\text{Radiation Force} = \frac{2\alpha I}{c} \qquad (2)$$

where F is a volumic force (N/m³), α is the tissue absorption coefficient (m⁴), I is the temporal average acoustic intensity (W/m²), and c is the speed of sound (m/sec). Deformation of the tissue was found with Young's modulus as in equation (3):

$$\varepsilon = \frac{\sigma}{E} \qquad (3)$$

assuming a Young's modulus of 576 kPa.

All analysis of data was done through functions (Student's t-test, one-way ANOVA, linear regression) provided within MATLAB.

Results

FUS Stimulation

Targeting of the sciatic nerve in anesthetized mice was done with an 18.5 MHz imaging probe, and was subsequently stimulated with a 3.57 MHz stimulation transducer. FIG. 1 is a diagram illustrating an exemplary embodiment of a system for modulating peripheral nerves in a subject using an ultrasound assembly according to the disclosed subject matter. FIG. 1 shows the targeting and positioning for both the stimulation and imaging transducer. FIG. 1 depicts the targeting of the ultrasound transducers on the sciatic nerve 155, as well as the position of the mouse leg 150 under the water bath 140 and stimulation transducer 102. B-mode images are acquired initially by switching out the transducer probe on the 3D positioner mount. The B-mode images are used to target the sciatic nerve, with nerve and bone highlighted in white circles in the inset of FIG. 1. Initially, a range of FUS parameters (0.7-5.7 MPa peak-negative-pressure (PNP), 15-100% duty cycle (DC), 1 kHz pulse repetition frequency (PRF), 0.8 ms-1 s stimulation duration) were employed to determine those that were efficacious in stimulating the sciatic nerve. Reported pressures in this Example for in vivo experiments account for skin and muscle attenuation. The range of these initial FUS parameters were determined from prior PNS and CNS stimulation studies. Lower pressures and duty cycles were investigated first, but EMG activity and visible muscle activation was only detected once pressures and duty cycles were above 3.2 MPa and 35% respectively (See Methods for full parameter testing protocol). Also of note, the electromagnetic field (EMF) produced from the transducer generated various artifacts such as signal depression, which can appear as a false positive response (FIG. 2). FIG. 2 is a graph demonstrating artifacts from EMF noise, where the lines indicate traces from EMG recordings. The thick black bars in FIG. 2 indicate the periods when ultrasound was applied. From these preliminary experiments, a set of parameters were found to successfully elicit EMG results: 3.2-5.7 MPa, 35-100% DC, 1 kHz PRF, 0.8-10.5 ms stimulation duration. For evaluation, the data were divided into two groups. The first pertaining to FUS stimulations with a total stimulation time of 0.8 ms, and a second with stimulation times between 1-10.5 ms. The varied stimulation times between 1-10.5 ms did not have a significant effect on EMG response delay (time between onset of FUS stimulation and EMG response) or peak-to-peak EMG signals (one-way ANOVA, $p=0.6934$, $p=0.5961$ respectively). While excitation of the sciatic nerve was possible at higher pressures/longer duration ($>100$ ms), gross examination of skin and surrounding muscle revealed tissue damage (change of color, consistency) in that range without the need for histological evaluation. The excitation associated with the visible damage was not reproducible after the first EMG response regardless of intra-trial pauses. The damage generated can be irreversible as shown in the positive control for histology (see Results: Histology).

Figure 3A:
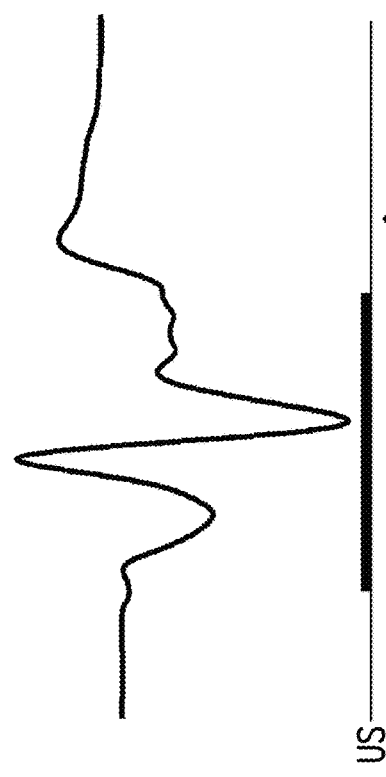
FIGS. 3A-3C are graphs showing typical EMG responses to FUS stimulation under the conditions described in Example 1.
Figure 3B:
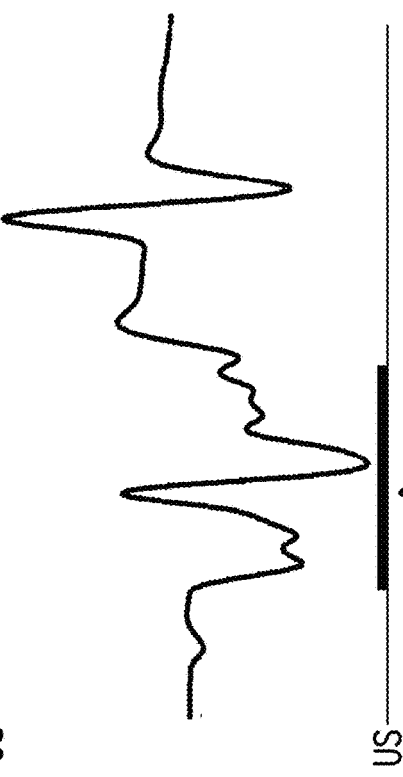
Figure 3C:
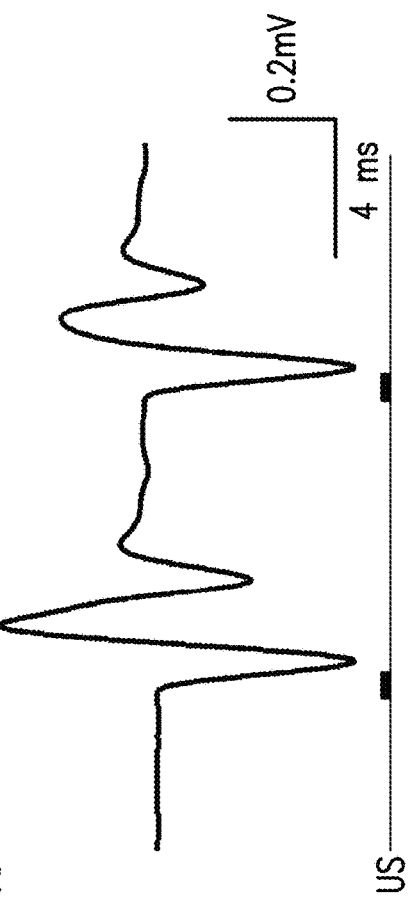

FIGS. 3A-3C are graphs showing typical EMG responses to FUS stimulation. The lines are the recorded EMG signals. The thick black bars indicate the periods when ultrasound was applied. FIG. 3A is a graph showing a single spike EMG response to FUS stimulation of the long duration group (1-10 ms stimulation duration). It shows a typical single spike EMG response to FUS stimulation of the sciatic nerve with a PRF of 1 kHz and an 8 ms stimulation duration. These were the most common responses observed ($n=63$) with the set of parameters defined above. Occasionally, a second EMG signal ($n=18$) was observed following the FUS stimulus, as shown in FIG. 3B. FIG. 3B is a graph showing a double spike EMG response to FUS stimulation of the long duration group. 83% of such secondary signals occurred when a 50% DC was utilized during FUS stimulation. When stimulating the sciatic nerve with a 35% DC, only this secondary EMG response was observed after stimulation had occurred ($n=7$). As seen in FIGS. 3A and 3B, these EMG responses during FUS stimulation were accompanied by the aforementioned EMF artifact. Reducing the stimulation duration to 0.8 ms with 100% DC (continuous wave), single EMG responses with reduced EMF noise could be elicited, as shown in FIG. 3C ($n=57$). FIG. 3C is a graph showing two EMG spikes for the short FUS stimulation duration group (0.8 ms stimulation duration). No EMG signals or observable muscle activation was detected using a DC less than 100% for the 0.8 ms stimulation group. There were no significant changes in peak-to-peak EMG responses with changes in stimulation duration for the 1-10.5 ms group (1-way ANOVA, $p=0.5961$). On average, the EMG responses for the 0.8 ms stimulation group were not significantly different from the EMG responses for the 1-10.5 ms stimulation group per each pressure (Student's t-test, $p=0.1044$; data are significantly different if $p<0.05$).

Figure 4:
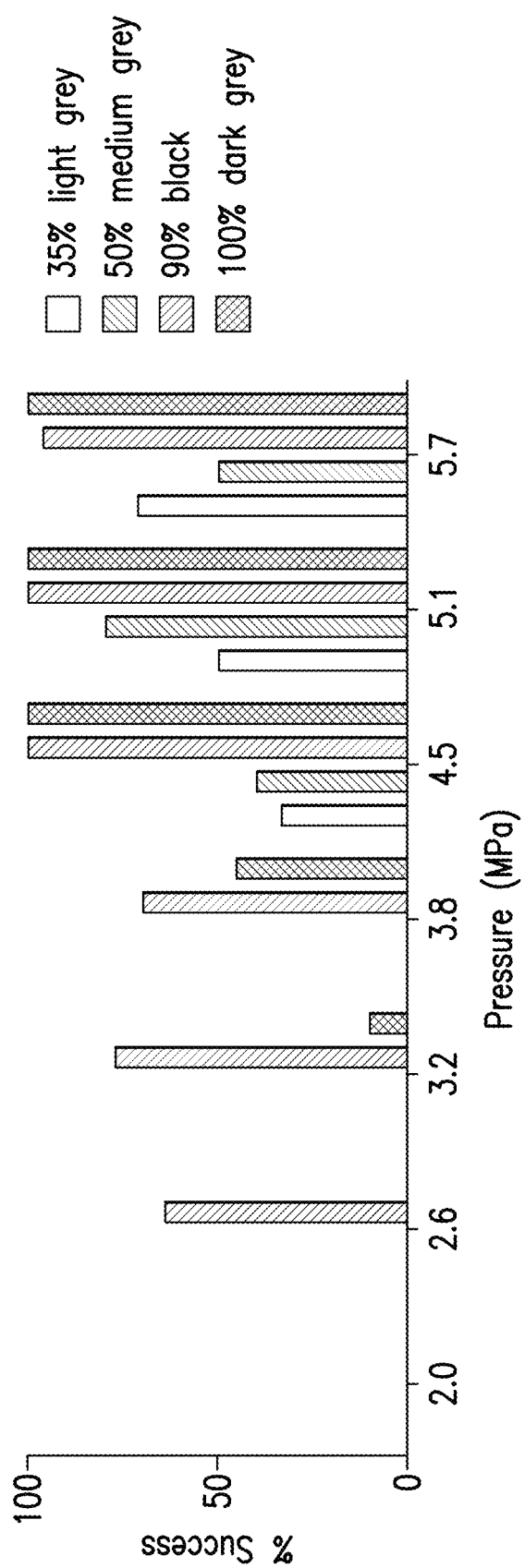
FIG. 4 is a diagram showing stimulation success rates.
Figure 5:
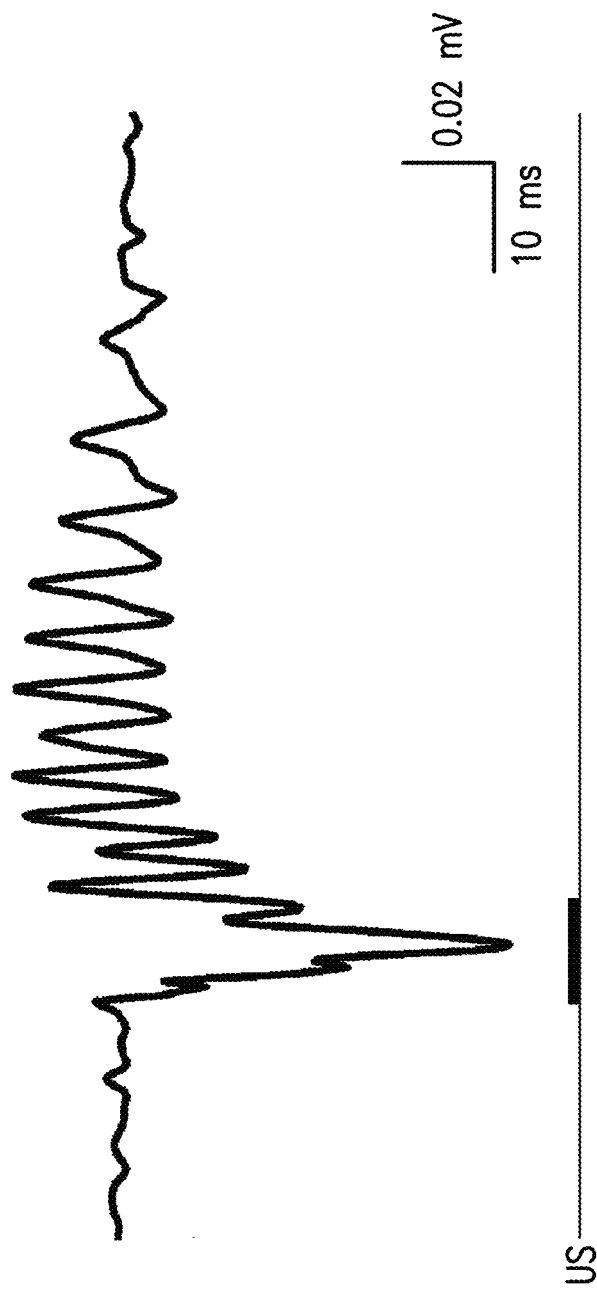
FIG. 5 is a graph demonstrating EMG response while stimulating the skin.

The success of stimulation for each parameter group is shown in FIG. 4. FIG. 4 is a diagram showing stimulation success rates. FIG. 4 shows success rate with pressure and pulse length. The light grey, medium grey, and black bars are from the long stimulation group (1-10.5 ms) while the dark grey bar is from the short stimulation group (0.8 ms). Success was determined as the ability to elicit subsequent EMG responses following initial EMG detection or observable muscle contraction. As shown with both the 0.8 ms and longer duration groups, success rates increased overall with pressure and pulse length. For both groups, there was a large decrease in success between the 4.5 MPa and 3.8 MPa groups (55 and 41%, respectively). Successful stimulation occurred at a higher rate for lower pressures (2.6-3.8 MPa) with the longer duration group, than for the same pressures in the 0.8 ms stimulation duration group. It was observed that following a stimulation without EMG activity (unsuccessful trial), a break period of 20-30 seconds improved the next stimulation success to 92% ($n=15$), suggesting a greater latency is needed for repolarization after multiple failed stimulations. Moving the FUS focal spot away from the targeted sciatic nerve eliminated both observable muscle activation and single spike EMG activity with fully anesthetized mice. Stimulation of the skin and muscle tissue at light planes of anesthesia did result in compound EMG activity shown in FIG. 5 ($n=80$), but never single spikes as observed with stimulation of the sciatic nerve. FIG. 5 is a graph demonstrating EMG response while stimulating the skin. The lines are traces from EMG recordings. The thick black bars indicate the period when ultrasound was being applied.

Figure 6:
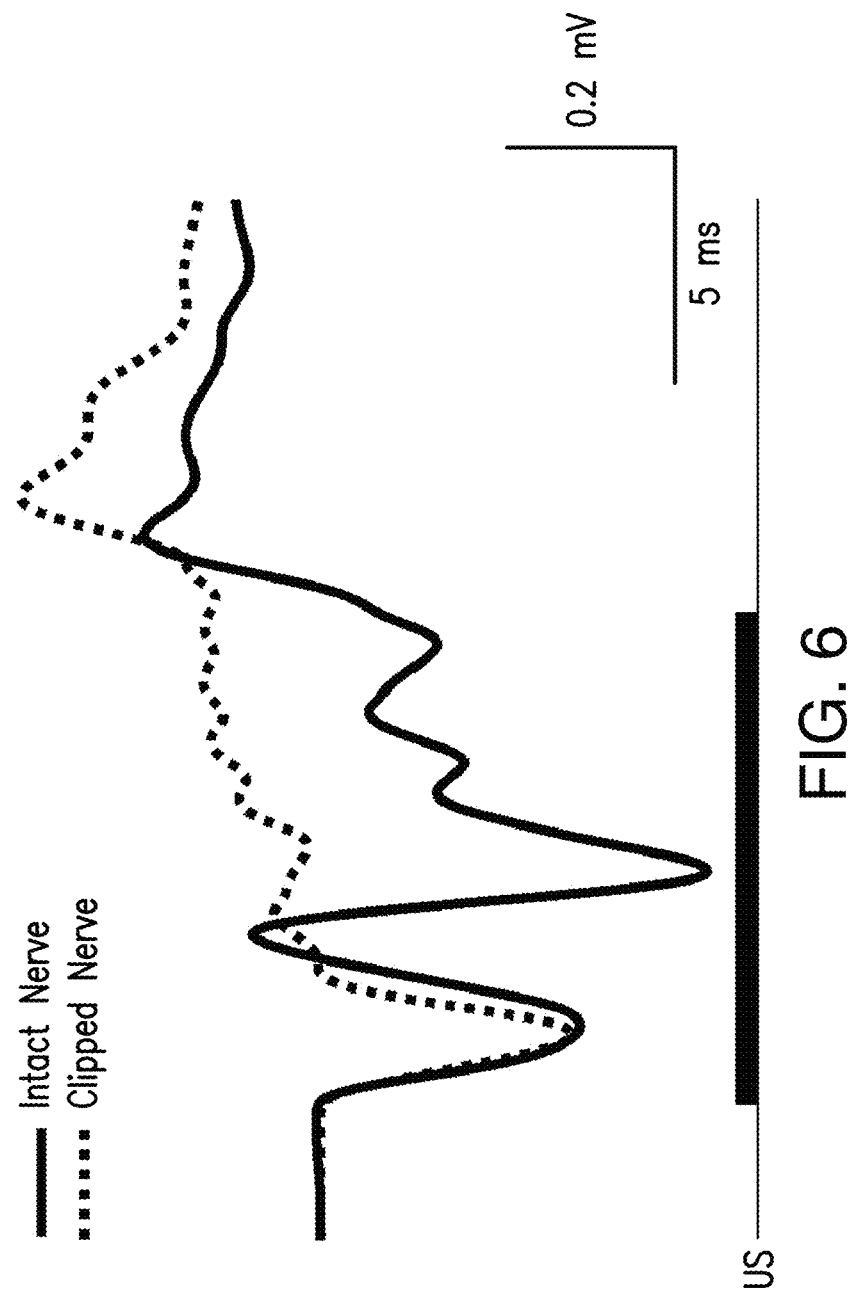
FIG. 6 is a graph showing EMG responses before and after nerve clip.

To verify EMG signals and muscle contraction occurred due to stimulation of the nerve and not the surrounding tissue, nerve transection experiments were conducted. After acquiring multiple ($n=20$) successful EMG responses, a small incision was made in the thigh muscle exposing the sciatic nerve. The nerve was then clipped downstream of FUS stimulation and the transducer was repositioned at the prior location of successful stimulation. Transection of the sciatic nerve abolished all EMG signals from FUS stimulation as shown in FIG. 6. FIG. 6 is a graph showing EMG responses before and after nerve clip. The solid line is the recorded EMG signal before nerve transsection while the dashed line is the EMG signal after the nerve had been transected. The black bar indicates the period when ultrasound was being applied.

Electrical Stimulation Comparison

Figure 7A:
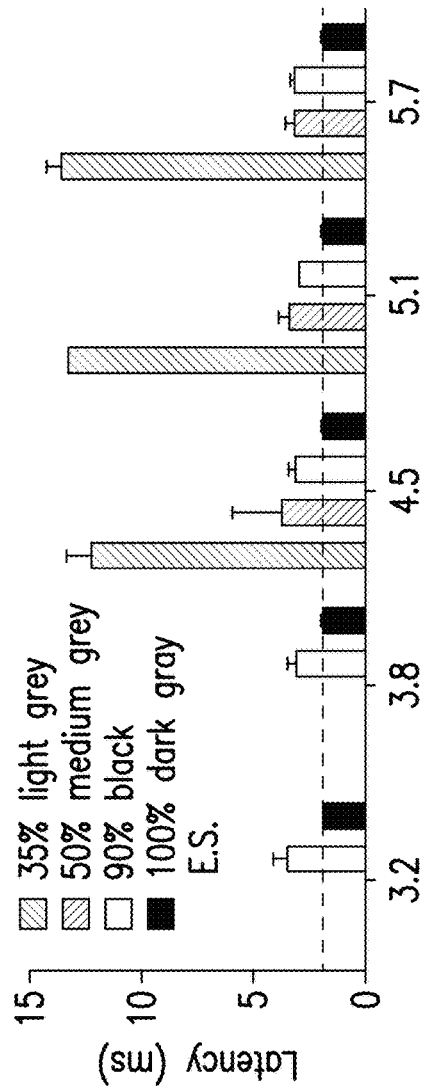
FIGS. 7A-7B are graphs comparing EMG signals between electrical and FUS stimulation.
Figure 7B:
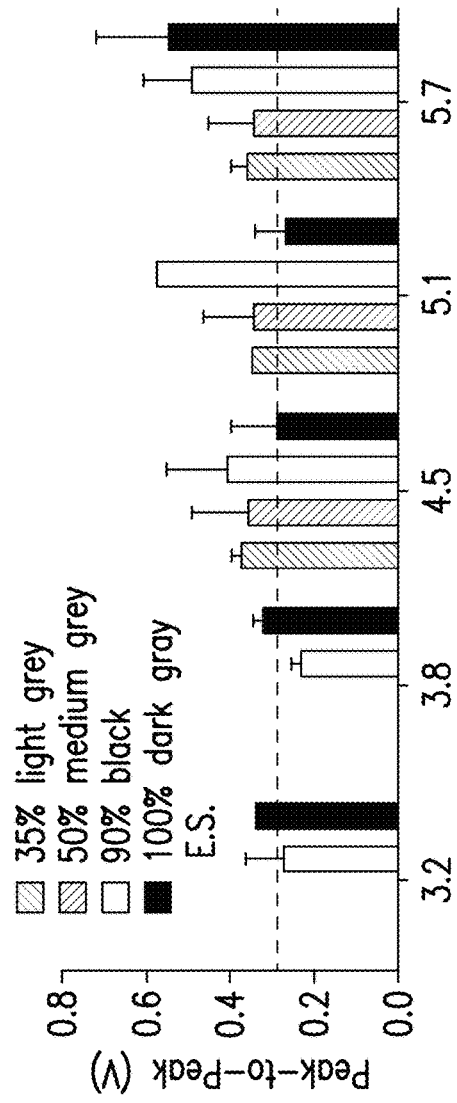

Electrical stimulation of the sciatic nerve was used both as a validation step for placement of the EMG electrodes in the tibialis anterior muscle initially as well as a benchmark for comparing the FUS responses to conventional methods. A range of electrical stimulation parameters were investigated (see Methods: Electrical Stimulation) to determine the parameters most similar to FUS stimulation. These parameters were selected from prior studies employing electrical stimulation to treat neuropathy. An electrical stimulation of 10 mA, 250 µs stimulation duration, and 5V generated similar peak-to-peak EMG spikes as that of the FUS stimulation response. FIGS. 7A-7B are graphs comparing EMG signals between electrical and FUS stimulation. The dotted horizontal bar indicates electrical stimulation ("E. S.") response. The light grey, medium grey and black bars are from the long stimulation group (1-10.5 ms) while the dark grey bar color bars are from the short stimulation group (0.8 ms). FIG. 7A shows the average delay from onset of stimulation to EMG signal and standard deviation for each pressure and duty cycle. FIG. 7A shows that the latency to the EMG signal was comparable for both the 0.8 ms and long/1-10.5 ms duration stimulation groups, except for the 35% DC subgroup, which was significantly slower than all other groups (Student's t-test, $p=6.1321e^{-36}$). As noted above, the 35% DC subgroup only generated EMG responses after FUS stimulation had ceased. The 0.8 ms stimulation duration group had the most consistent delay and was not significantly different than that of the electrical stimulation group (Student's t-test, p=0.0593). FIG. 7B shows the average peak-to-peak and standard deviation EMG for each pressure and duty cycle.

Behavioral Testing

Figure 8:
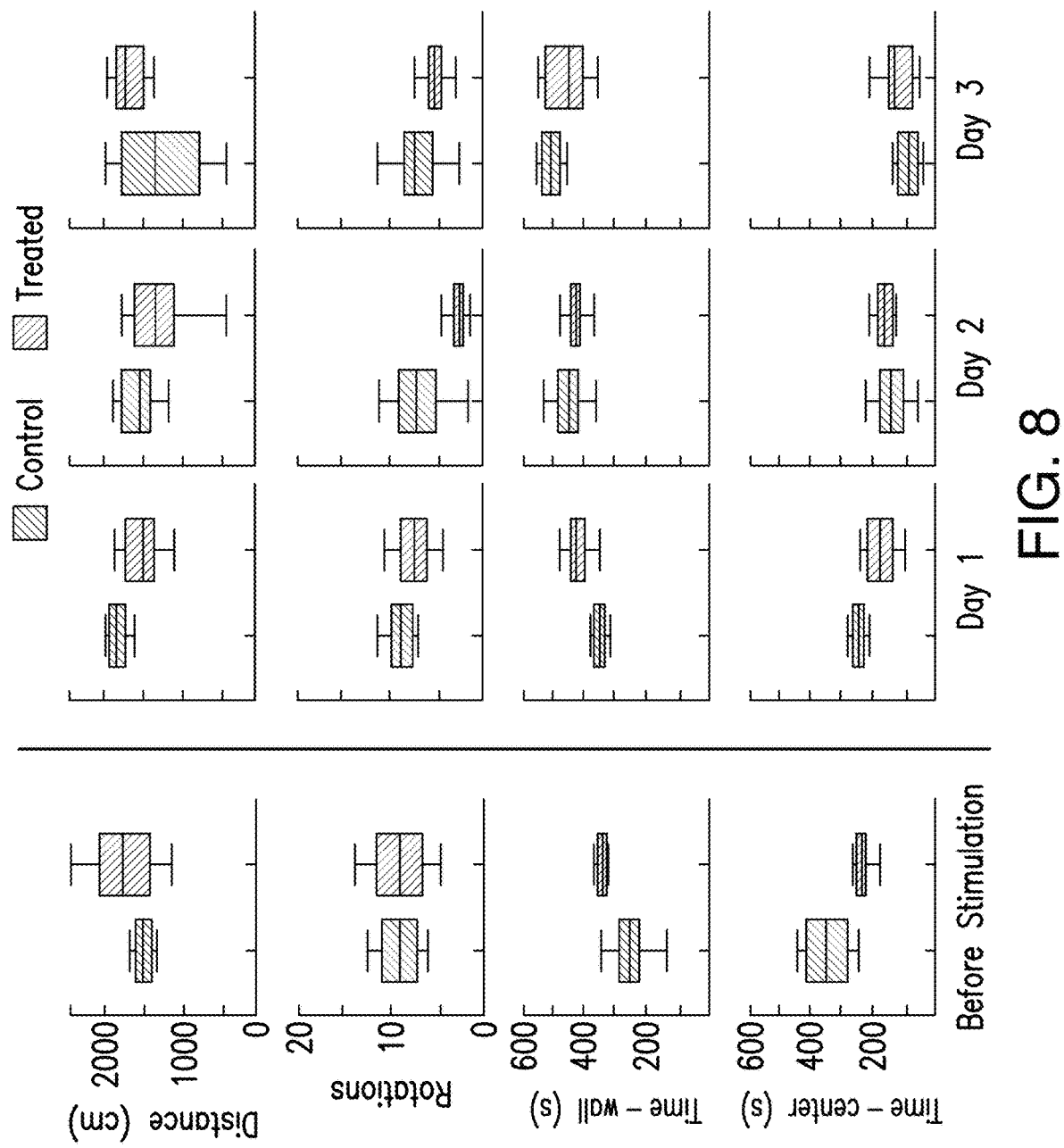
FIG. 8 is a series of graphs showing behavioral testing data in accordance with Example 1 of the present disclosure.

An open field test (30 cm$^2$ opaque square box) was utilized to assess short term damage to the nerve and surrounding tissue from the FUS stimulation. Mice were recorded one day prior and three days following FUS stimulation. The total distance traveled and number of rotations to the ipsilateral side of FUS stimulation were monitored as a decrease in distance traveled and ipsilateral rotations can indicate damage. For example, FIG. 8 is a series of graphs showing behavioral testing data. Comparison between the stimulated group (light grey) and the control group (black) for each day is displayed in FIG. 8. Each row is a separate test: time spent at the wall, time spent in the center, total distance traveled and number of rotations. There were no significant deviations between the day before stimulation, nor the control groups. As shown in FIG. 8, distance traveled for mice that received FUS stimulation did not significantly change from the control group, nor from their average distance traveled on day −1 (one-way ANOVA, p=0.4533). The average number of rotations towards the ipsilateral side of FUS stimulation also did not significantly change as compared to the days following FUS stimulation and the control group (FIG. 8, one-way ANOVA, p=0.1695). Their time spent in the center and along the walls of the open field test was also monitored as a determinant of their anxiety levels. If the FUS stimulation had caused discomfort, but not to the point of generating detectable damage with the metrics employed above, monitoring their activity relative to their position in the box could be used to determine if they were more anxious following the procedure. FIG. 8 also shows the stimulated group does not significantly differ from the trends of the control group, as the mice spend less time overall within the center of the box and more time in the outside of the box over the time course of the experiment (Student's t-test, all groups p>0.05). These behavioral results indicate that the FUS stimulation parameters that were successful at eliciting EMG responses are also safe for short term applications.

Histology

Figure 9A:
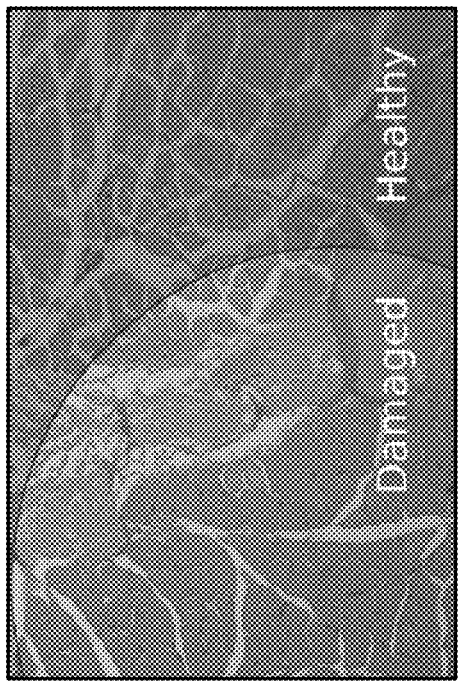
FIGS. 9A-9C are graphs showing H&E Histology and thermal measurements for FUS Stimulation.
Figure 9B:
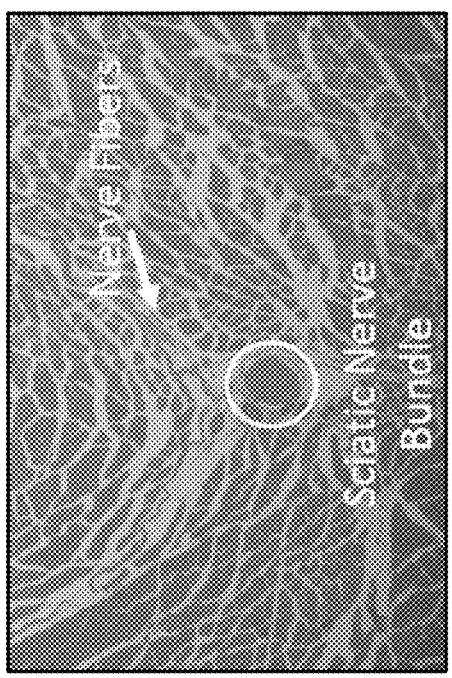

H&E staining of the sciatic nerve and surrounding tissue in the FUS targeted area were evaluated with a blinded study for damage (n=8 FUS stimulation, n=8 negative control, n=1 positive control. See Methods for full parameters). Damage was defined as red blood cell extravasation, abnormal cell morphology, inflammation, and destruction of cellular membranes. FIGS. 9A-9B are images of the H&E Histology. FIG. 9A is a an image showing the sciatic nerve bundle and surrounding neural and muscle tissue for the FUS stimulated group with parameters found for successful EMG and muscle activation. FIG. 9A shows the FUS targeted area when using parameters found successful to elicit EMG responses. No damage was observed for any of stimulated mice samples, nor with the negative controls (no FUS stimulation). Damage was detected for the positive control (5.4 MPa, 90% DC, 1 kHz PRF, 0.5 s stimulation duration) as shown in FIG. 9B. FIG. 9B is an image of the positive control group showing damaged areas by applying FUS stimulation for 0.5 s. Red blood cell extravasation, inflammation, and cell membrane destruction was found in the stimulated region, while areas neighboring the targeted region were unaffected, demonstrating the target specificity of the FUS stimulation. As with the behavioral results, these results indicate that the FUS parameters found efficacious for eliciting EMG response while stimulating the sciatic nerve were safe.

Thermocouple

Figure 9C:
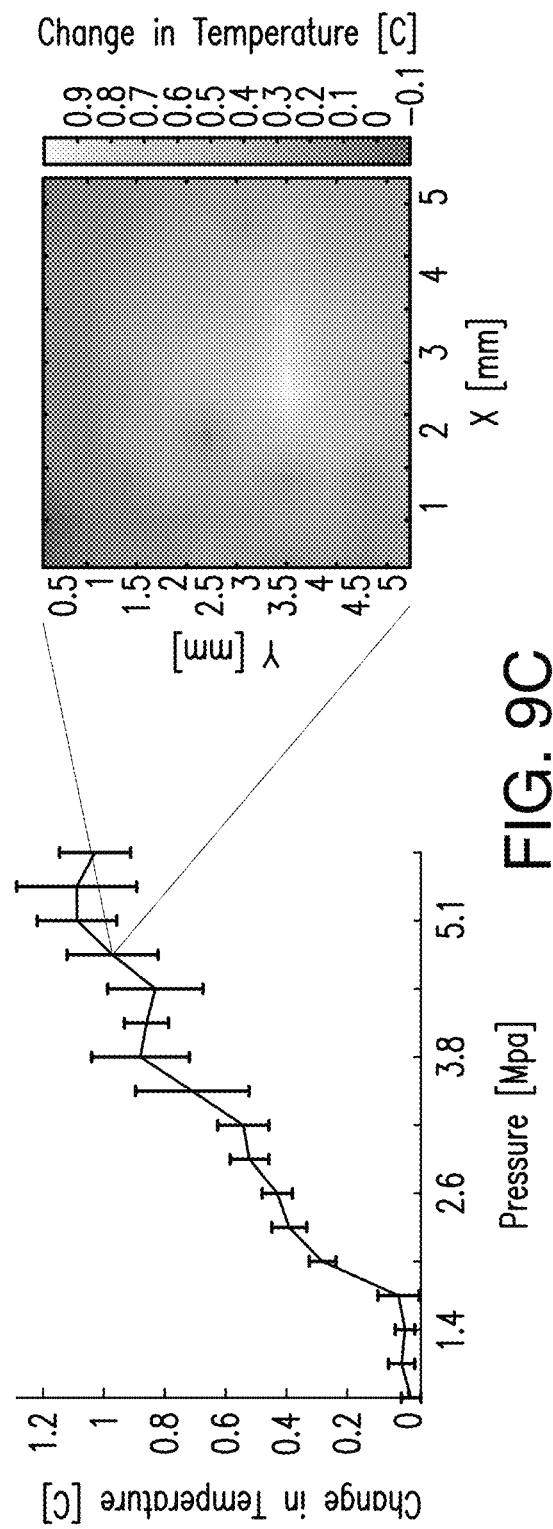

To determine if the FUS stimulation elicited a thermal effect, thermocouples were embedded in an ex vivo mouse hind limb adjacent to the sciatic nerve. The mouse limb was pinned to a dissection tray filled with degassed water and maintained at room temperature (21° C.). FIG. 9C shows the average ±s.d. temperature for the following FUS parameters: 0.7-5.3 MPa, 90% duty cycle, 1 kHz PRF and provides a plot of pressure vs average ±s.d. temperature increase in an ex vivo mouse hind limb from baseline (room temperature 21° C.). The inset of FIG. 9C includes a raster plot of temperature increase in an ex vivo mouse hind limb during FUS stimulation at a PNP of 4.5 MPa. Stimulation at the higher pressures exhibited a 1.09° C. increase in temperature of the ex vivo limb with an overall range of 0-1.09° C. The raster of the temperature during FUS stimulation at 4.5 MPa, shows the peak temperature increase was at the focal area, but there was local heating surrounding the focal area due to the femur being within the raster area. These increases in temperature decayed to baseline within 14±2 seconds on average (n=5). This small change in temperature recorded was significantly lower than prior reported values for inhibition of peripheral neurons during ex vivo experiments which required temperature increases of up to 20° C.

Radiation Force

Utilizing the pressures found successful for eliciting EMG responses, the acoustic radiation force generated from the transducer was capable of deforming the tissue in the targeted area relative to the adjacent region. The acoustic radiation force was measured using a force balance to determine the total power from the transducer and then converted to determine the deformation at the focal region. Assuming a Young's modulus of 576 kPa for neural tissue, the deformation varied with applied input voltages from 14-422 μm (0.1 V/0.7 MPa, 0.9 V/5.7 MPa respectively). Table 1 details the power output and deformation for all pressures utilized within this Example. The displacement generated by the FUS parameters employed in this study was large enough to facilitate the firing of the action potential to elicit EMG activity according to prior work.

TABLE 1

Values for power output, theoretical deformation, pulse energy and temperature increase for applied pressures.

| Pressure (PNP, MPa) | Power (W) | Displacement (μm) | Pulse Energy (mJ) | Temperature Increase (C. °) |
|---|---|---|---|---|
| 0.7 | 3.2 | 8.5 | 0.5 | 0.01 |
| 1.4 | 12.8 | 34.1 | 1.9 | 0.01 |
| 2.0 | 31.0 | 82.7 | 4.6 | 0.28 |
| 2.6 | 54.7 | 146.0 | 8.1 | 0.43 |
| 3.2 | 85.2 | 227.1 | 12.5 | 0.54 |
| 3.8 | 97.8 | 260.6 | 14.4 | 0.88 |
| 4.5 | 118.1 | 314.7 | 17.4 | 0.83 |

TABLE 1-continued

Values for power output, theoretical deformation, pulse energy and temperature increase for applied pressures.

| Pressure (PNP, MPa) | Power (W) | Displacement (μm) | Pulse Energy (mJ) | Temperature Increase (C. °) |
|---|---|---|---|---|
| 5.1 | 138.4 | 368.7 | 20.4 | 1.09 |
| 5.7 | 158.6 | 422.8 | 23.4 | 1.01 |

DISCUSSION

This Example demonstrates successful in vivo FUS stimulation of the peripheral nervous system. Prior conventional techniques such as electrical stimulation or drug therapies are, respectively, either invasive or untargeted. Drug therapies are the most common treatments, but with all drug approaches there is the possibility for unwanted systemic side effects. Throughout the lifetime of implantable electrical stimulation devices, complications can arise from surgery, immune response to implant, and damage to the nerve from repeated electrical stimulation. FUS stimulation of the PNS is both non-invasive and targeted, reducing the complications for treatment of damaged peripheral nerves and the overall cost of treatment as surgery is not necessary. For at-home transdermal electrical stimulation systems, patients have reported the stimulation could not penetrate deep enough to reach the target area, along with irritation during stimulation. With a FUS system, these issues could be resolved as the target depth could be tailored using a multi-element array and varying the parameters applied. Since ultrasound is employed for the targeting of the nerve, an all-in-one system for targeting and stimulation of the peripheral nerve can be used, and with training, an at-home system could be used by patients, allowing for treatment without the need for travel to the clinic, reducing the overall financial and temporal costs of the treatment compared to conventional techniques that require multiple tests to determine therapy outcomes.

The success of the technique ranged from 16%-100% depending on the FUS parameters employed, demonstrating the reproducibility of this technique. While some of the success rates are lower than that for electrical stimulation (100% success), the mechanisms are fundamentally different. Electrical stimulation of an axon activates the voltage gated ion channels in the nodes of Ranvier generating an action potential. With ultrasound, the stimulation is fundamentally a mechanical force.

In this Example, it is hypothesized that the mechanical forces from FUS are being converted into an electrical signal by forcing open the voltage gated ion channels in the nodes of Ranvier. The direct mechanics of this conversion are unknown, but the findings presented herein indicate that the generation of the action potential occurs with onset of FUS stimulation. The short 0.8 ms stimulation duration elicited EMG responses with 100% success for pressures ranging from 4.5-5.7 MPa. These pressures correspond to a theoretical tissue displacement of up to 422 μm. Prior studies have shown mechanically stimulating a peripheral nerve axon can elicit an action potential with a deformation of only 10-60 μm. These studies used unmyelinated axons which are easier to stimulate, but here the nerve tissue is deformed orders of magnitude greater. While mechanosensitive ion channels exist on cell bodies, they are not present on the axon of the naïve sciatic nerve. Thus, with the lack of FUS activated mechanosensitive ion channels, it can be concluded that the deflection from the acoustic radiation force generates displacement of the axon, forcing opening of the voltage-gated ion channels located at the nodes of Ranvier. Prior work demonstrated stimulation of an ex vivo frog sciatic nerve by both ultrasound and mechanical stimulation, postulating the initial deformation of the nerve was the impetus of action potential generation. Other FUS studies have postulated intra-membrane cavitation and oscillation of bubbles within the membrane could change the membrane capacitance, thus triggering the cell to fire an action potential. The use of harmonic motion imaging will be explored to verify deformation in vivo during FUS stimulation as well as the detection of cavitation in future experiments.

Current ex vivo and in vitro reports on FUS PNS modulation are divided between thermal or mechanical effects driving the neuromodulation. Thus far, thermal effects are associated with inactivation of the stimulated nerve while mechanical effects are associated with the activation of the nerve. With the thermocouple experiments, the stimulation effects were verified as not due to temperature increase. The maximum temperature increase with the highest pressures/longest durations only had a temperature change of 1.09° C. in ex vivo tissue. Temperature increases of 14-20° C. were needed in prior work stimulating excised peripheral nerves before the action potential was inhibited. Even with a thermal decay time with an average of 6 seconds the increase in temperature at the sciatic nerve in vivo with the FUS parameters that were found efficacious does not necessarily generate a thermal increase of a magnitude required for inhibition. Thus, the in vivo experiments agree with the ex vivo literature stating excitation of the PNS is a mechanical, not thermal effect.

Comparison of FUS stimulation to conventional electrical stimulation shows that the latency of the EMG response for the 0.8 ms stimulation duration group was not significantly different than that of the electrical stimulation group. Although the stimulation constitutes a different mechanism, the findings indicate the mechanical stimulation to be as temporally efficient as with electrical stimulation. FUS stimulation responses were strong enough to elicit EMG spikes comparable to that of electrical stimulation and visible muscle contraction was recorded. The results demonstrate FUS can potentially serve as an alternative or complementary treatment to various patient conditions that are currently treated with electrical stimulation at peripheral nerve sites, like chronic pain and incontinence.

Investigation of the short-term physiological effects of FUS stimulation on the sciatic nerve revealed no detectable damage with either histology or behavioral testing. For many electrical stimulation therapies to treat peripheral nerve damage, device implantation and removal can generate damage to the nerve or surrounding tissue. The blinded histological examination study did not detect any RBC extravasations, nor changes in cellular morphology of the surrounding tissue for FUS parameters that were found successful for stimulation, demonstrating the technique is safe. Open field testing did not indicate any damage to the sonicated limb, behavior in mice after the stimulation was not significantly different from that of the control or baseline groups.

Overall, this example demonstrates FUS stimulation of the sciatic nerve in vivo and provides a range of FUS parameters that have been determined to successfully activate peripheral nerves and to elicit EMG activity downstream of FUS stimulation, as well as the abolishment of EMG signal when the nerve is transected. Safety experiments did not indicate any short-term damage to the nerve or the surrounding tissue. Recorded EMG signals were comparable to those generated using conventional electrical stimulation methods, indicating FUS stimulation can be a non-invasive alternative to electrical stimulation for peripheral nerve excitation. FUS thus has the ability to both excite and inhibit neuronal activity and can be a powerful tool to target multiple nerve types including the vagus, which has the potential to treat multiple diseases such as epilepsy, depression, and metabolic disorders. These results support further investigation of FUS-based techniques as a non-invasive and safe alternative to conventional treatment of electrical stimulating peripheral nerve sites.

Figure 10:
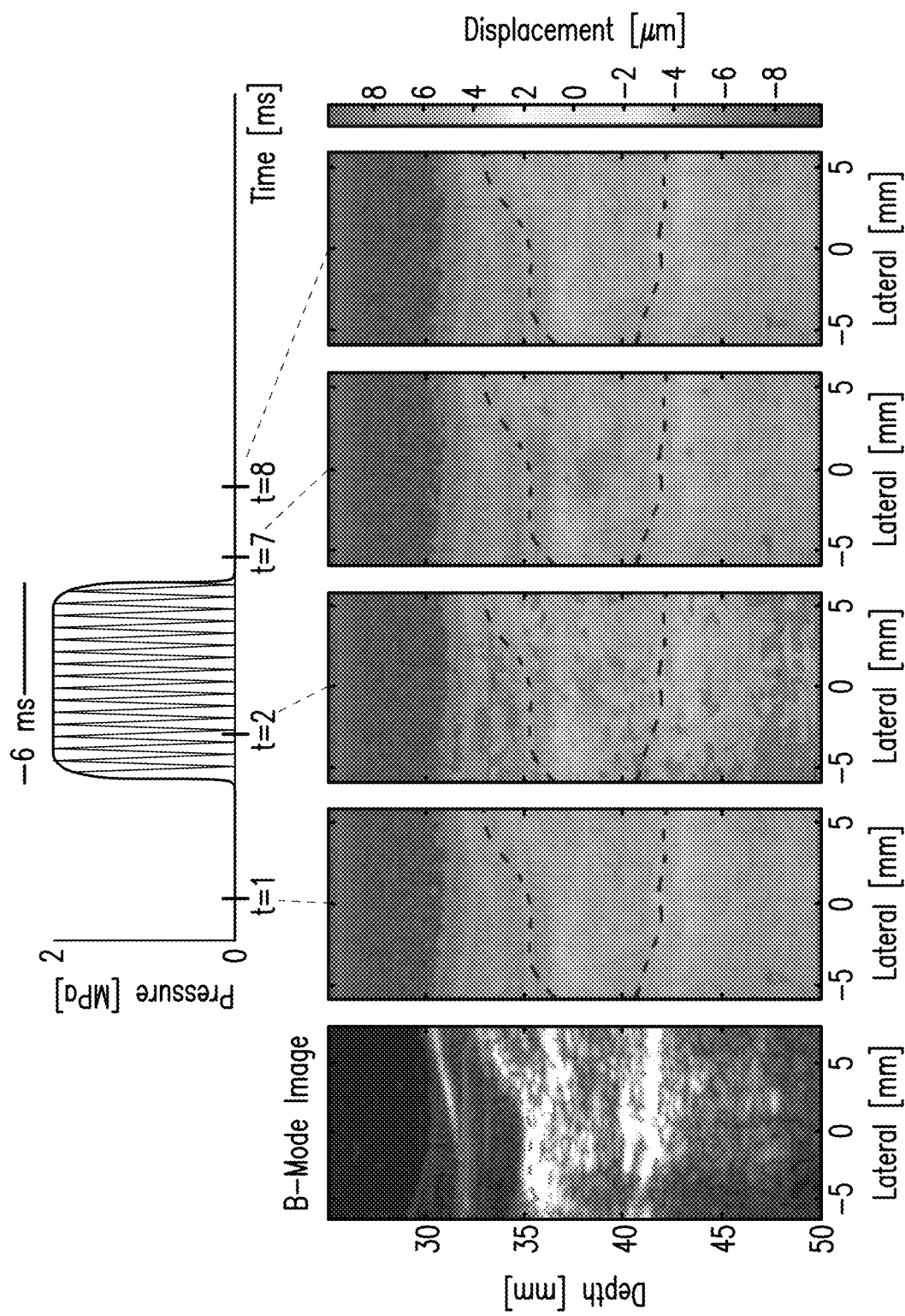
FIG. 10 is a diagram showing displacement maps overlaid on the B-mode images in a mouse in vivo in accordance with Example 2 of the present disclosure.

Example 2: Imaging of Tissue Displacement During Focused Ultrasound Neuromodulation In Vivo This Example provides methods and systems for imaging of tissue displacement during focused ultrasound neuromodulation in vivo.
Background, Motivation, and Objective FUS has been shown to modulate neural activity in the brain. Feasibility of FUS modulation of peripheral nerves has been shown in vivo, as described in Example 1. However, the mechanism of FUS on the PNS is not known and it is desirable to image modulated nerves in vivo to study the mechanism. Moreover, methods of imaging nerves in vivo can provide an image-guided approach to modulation monitoring. In this Example, a new transducer was designed that incorporates both the FUS transducer and an imaging array that can simultaneously image the mechanical perturbation of the tissue during modulation in vivo.
Methods The FUS stimulation system consists of a 96-element, 4.5 MHz HIFU therapeutic ultrasound transducer confocally aligned with a 104-element, 7.8-MHz, pulse-echo imaging transducer. The pulse length was equal to 6 ms and in vivo mice were used to determine feasibility. Activation of the sciatic nerve in the upper thigh of the mouse at 5 different locations were induced with the same parameters previously reported. A Verasonics Vantage was used to acquire 200 RF frames at a 10 kHz pulse repetition frequency and 1D cross-correlation with a 20 lambda window and 90% overlap was applied to image the inter-frame axial displacement before, during, and after modulation.
Results and Conclusions Displacement maps overlaid on the B-mode images are shown in an example of a mouse in vivo in FIG. 10. FIG. 10 is a diagram showing displacement maps overlaid on the B-mode images in an example of a mouse in vivo. Before FUS, no displacement was registered. Once FUS was applied (at 2 ms), downward displacement is detected with the highest displacement at the focus of the FUS beam. During modulation, the average peak displacement at the focus was 9.8 microns with the parameters used to induce sciatic nerve stimulation. After FUS is stopped (at 7 ms), displacement steadily decreases during 0.5-0.8 ms before complete recovery of the tissue. These findings indicate that FUS neuromodulation is associated with the radiation force effect and therefore its successful application is dependent upon sufficient displacement generation.

Figure 11:
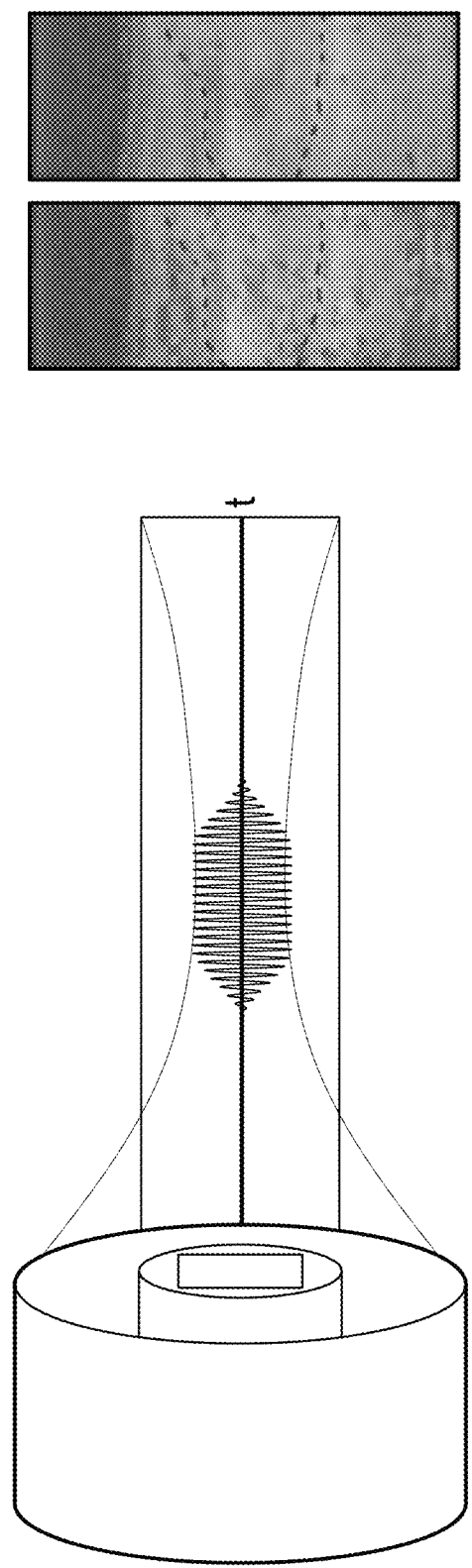
FIG. 11 is a diagram depicting stimulation and imaging parameters, as well as tracking sequences.
Figure 12:
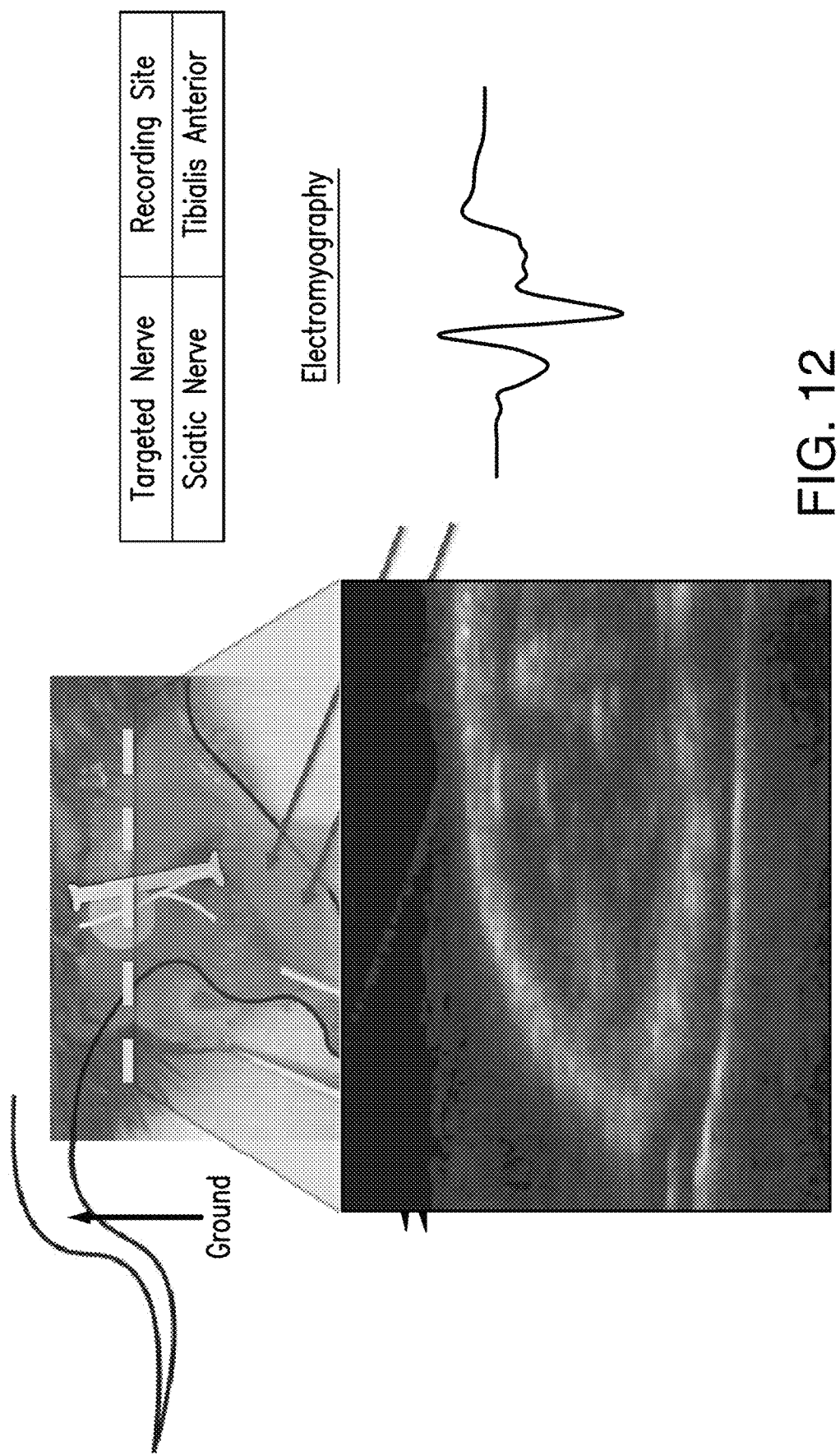
FIG. 12 is a diagram showing targeted nerve and recording site.
Figure 13:
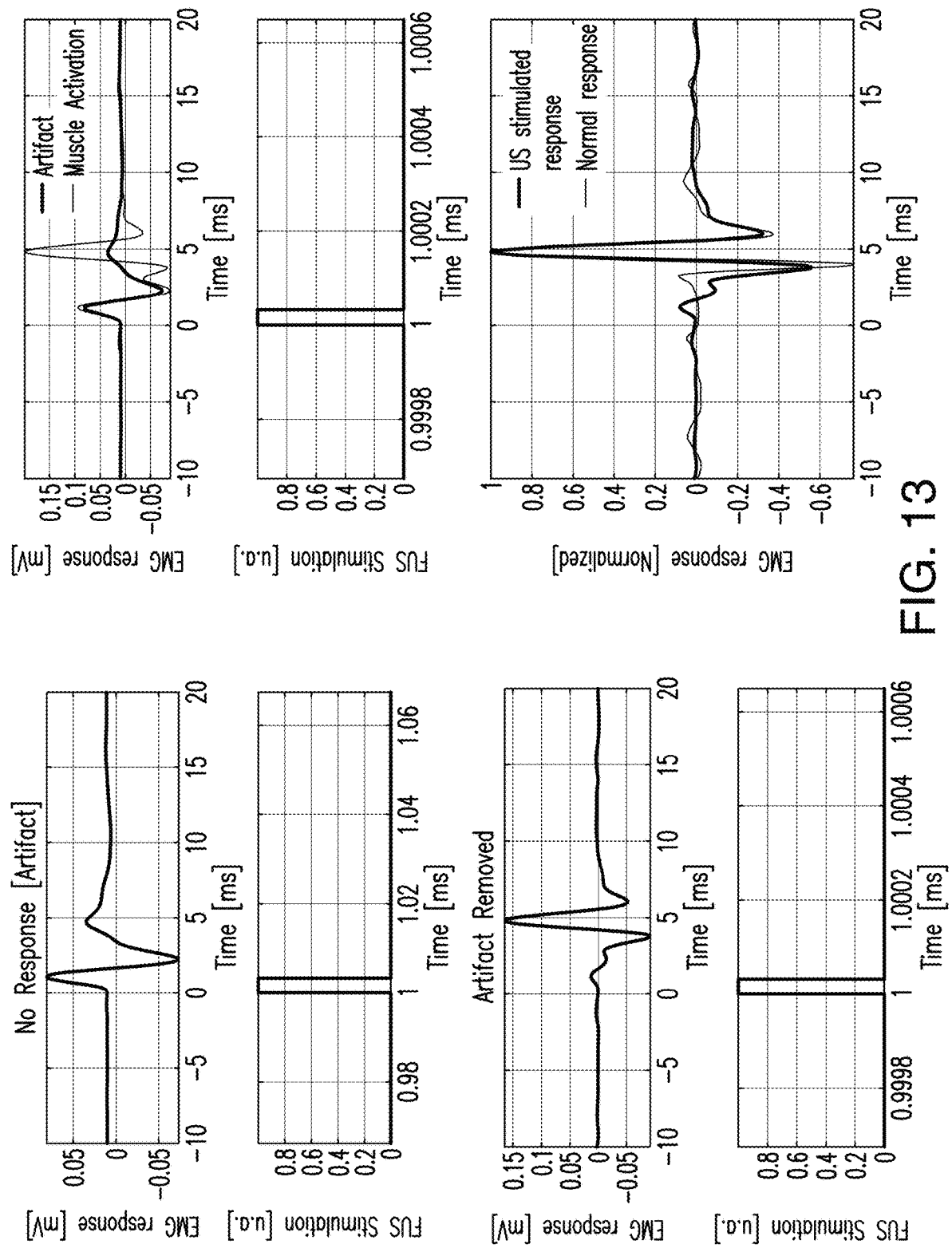
FIG. 13 is a graph showing EMG responses after removal of artifact and comparison to normal electrical stimulation responses.

FIG. 11 is a diagram depicting stimulation and imaging parameters, as well as tracking sequences and FIG. 12 is a diagram showing targeted nerve and recording site. FIG. 13 is a graph showing EMG responses after removal of artifact and comparison to normal electrical stimulation responses. It demonstrates that the ultrasound stimulated response is similar to the normal response, indicating that activity is induced in nerves rather than muscles.

Figure 14:
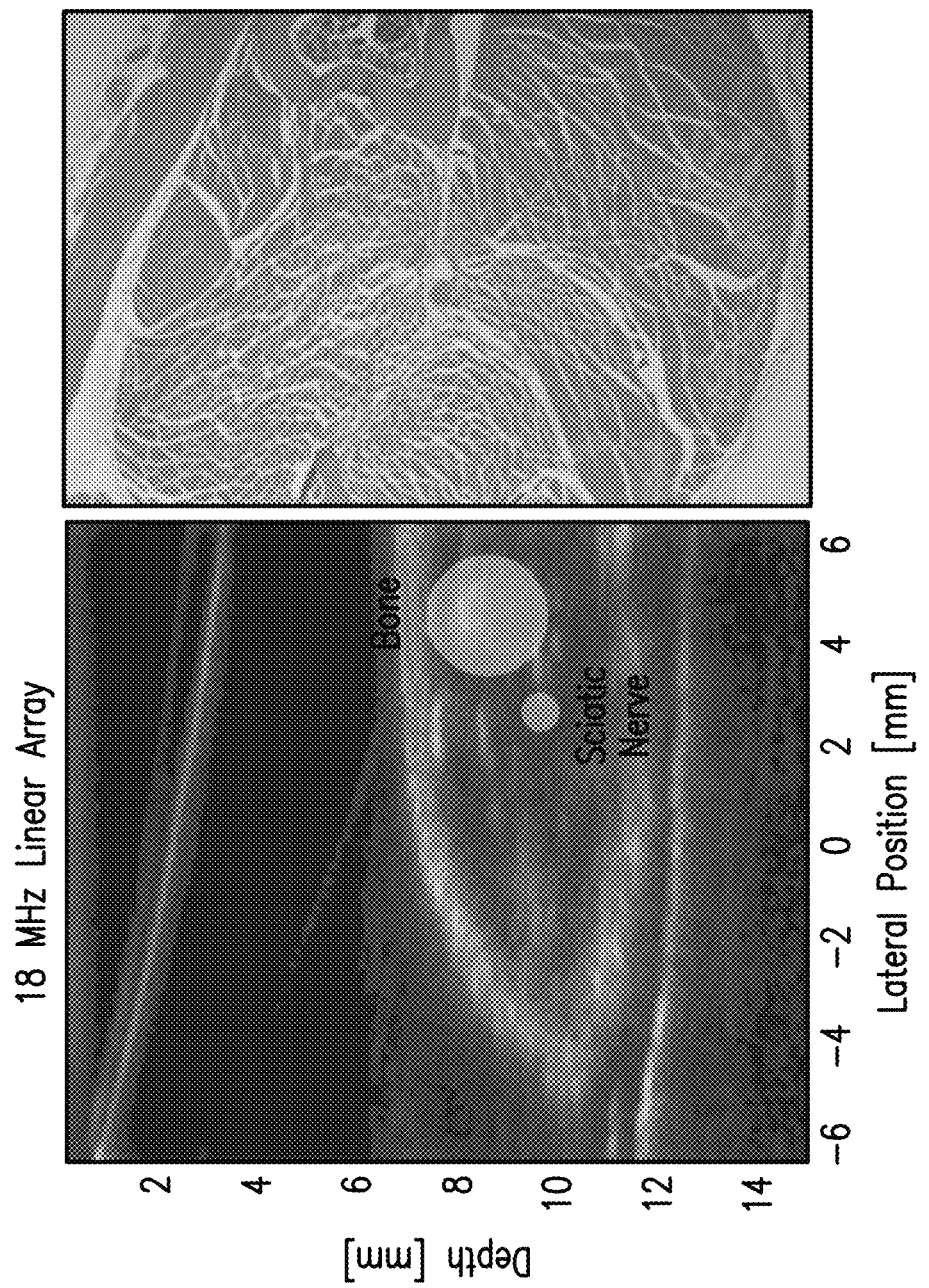
FIG. 14 is a diagram demonstrating area of activation in relation to bone.
Figure 15B:
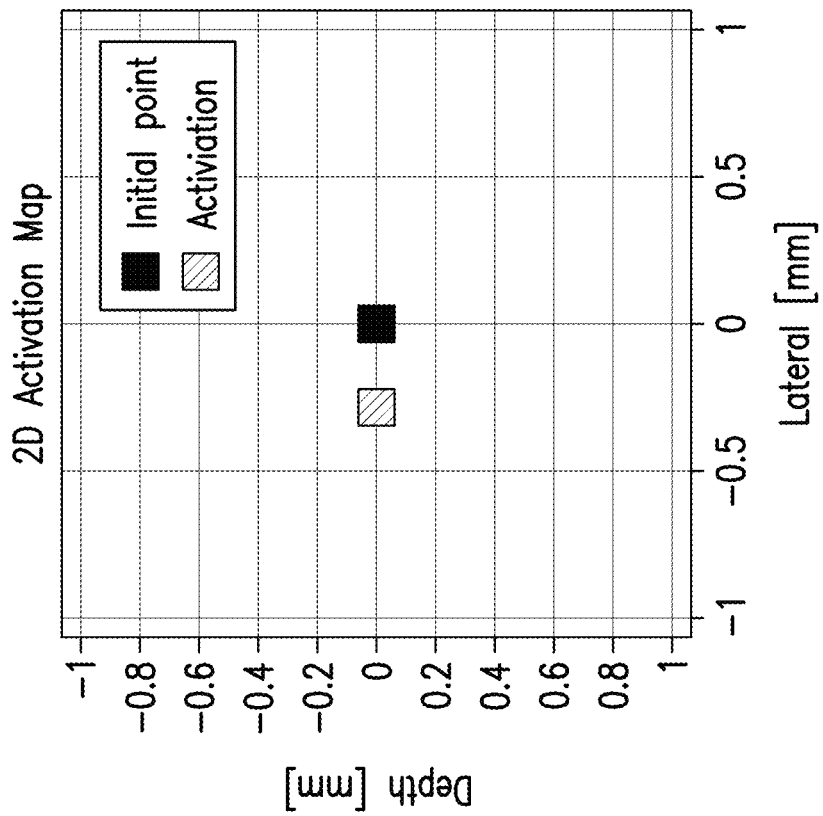
FIG. 15B is a graph showing areas of activation after the initial point was positioned at site of activation for finer raster scan.
Figure 15A:
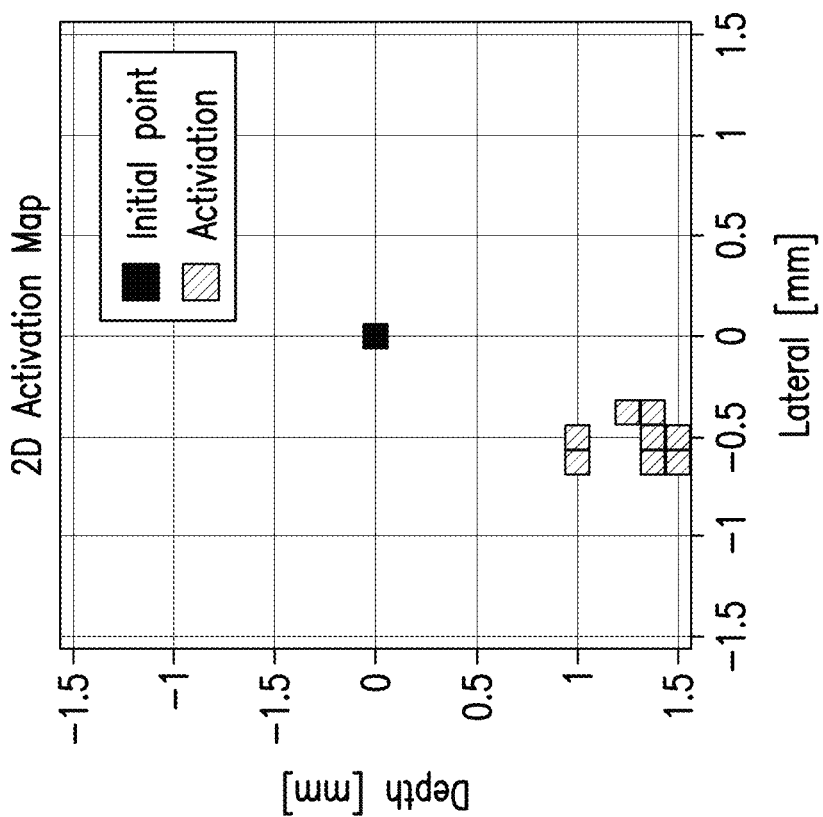
FIG. 15A is a graph showing areas of activation that correspond with sciatic nerve location relative to bone.

FIG. 14 is a diagram demonstrating area of activation in relation to bone. FIG. 15A is a graph showing areas of activation that correspond with sciatic nerve location relative to bone. FIG. 15B is a graph showing areas of activation after the initial point was positioned at site of activation for finer raster scan. These data show localized activity where nerve should be in relation to bone.

Figure 16A:
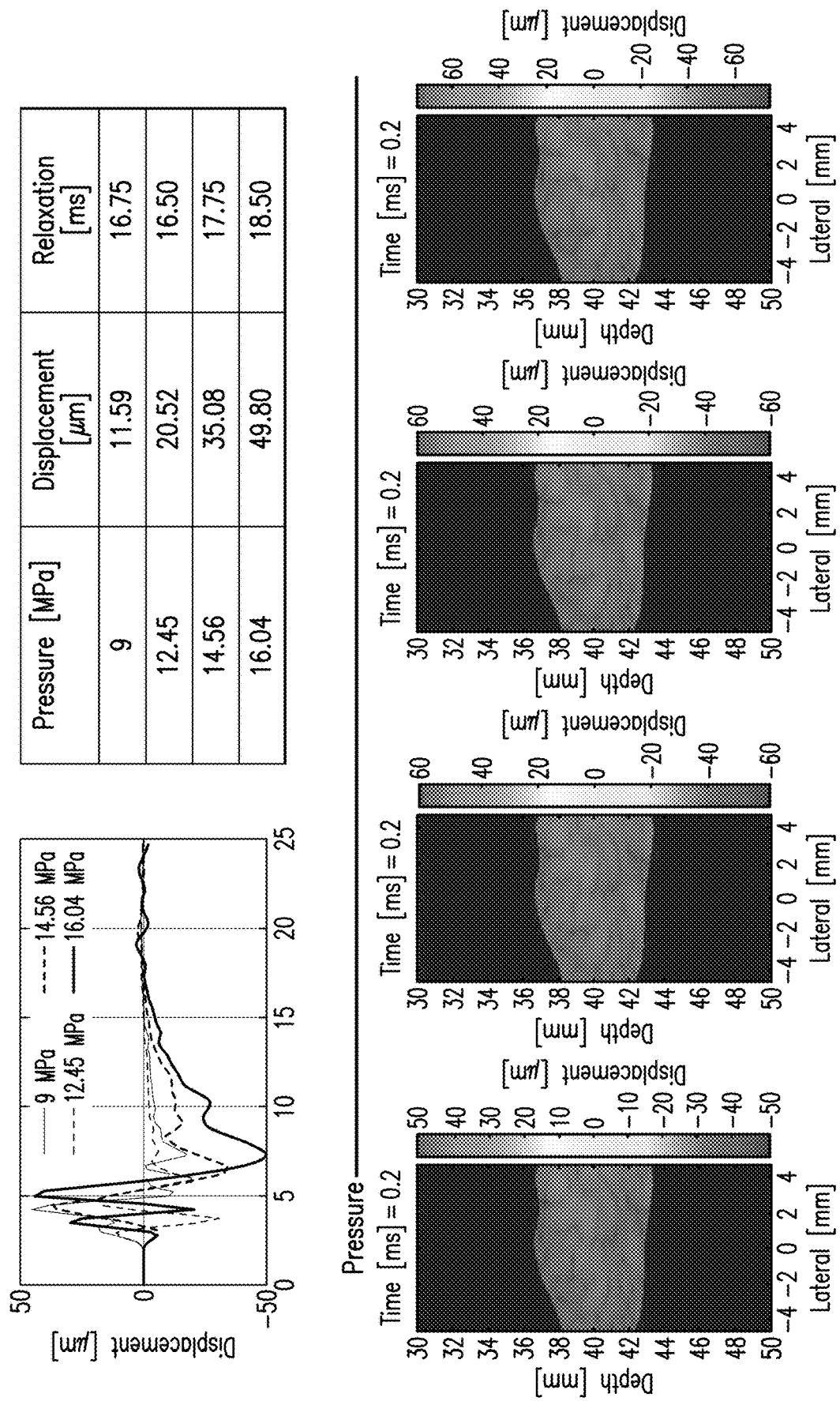
FIG. 16A is a graph showing displacement imaging modulation with increasing pressures.
Figure 16B:
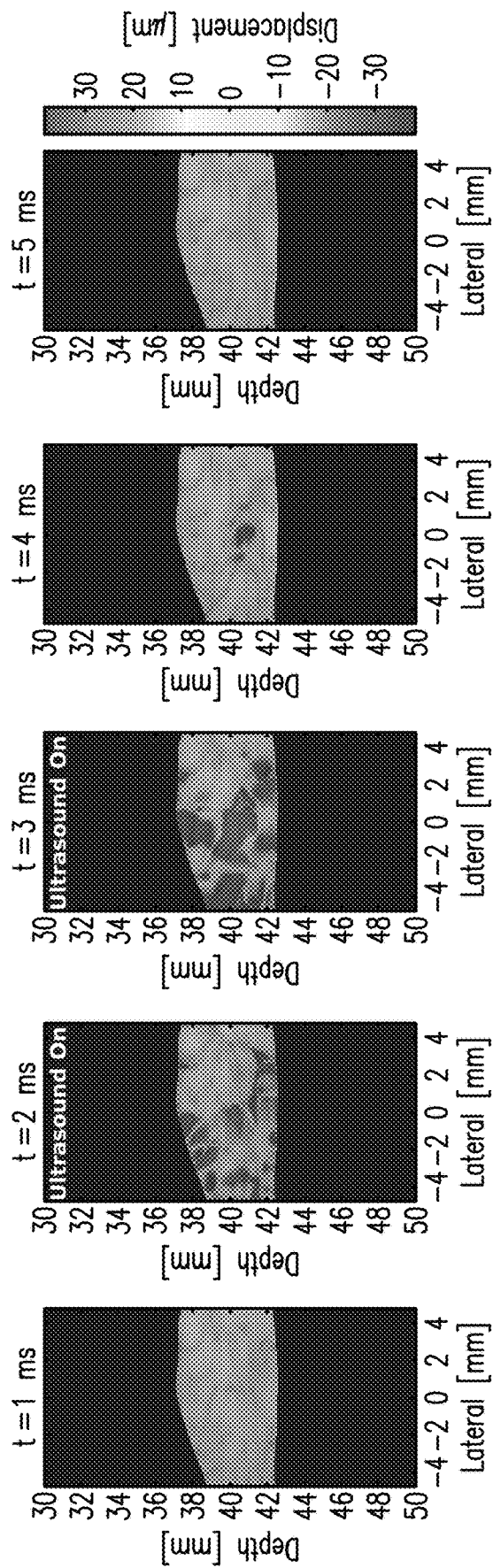
FIG. 16B is a graph showing individual frames of displacement imaging with 9 MPa pressure.
Figure 17:
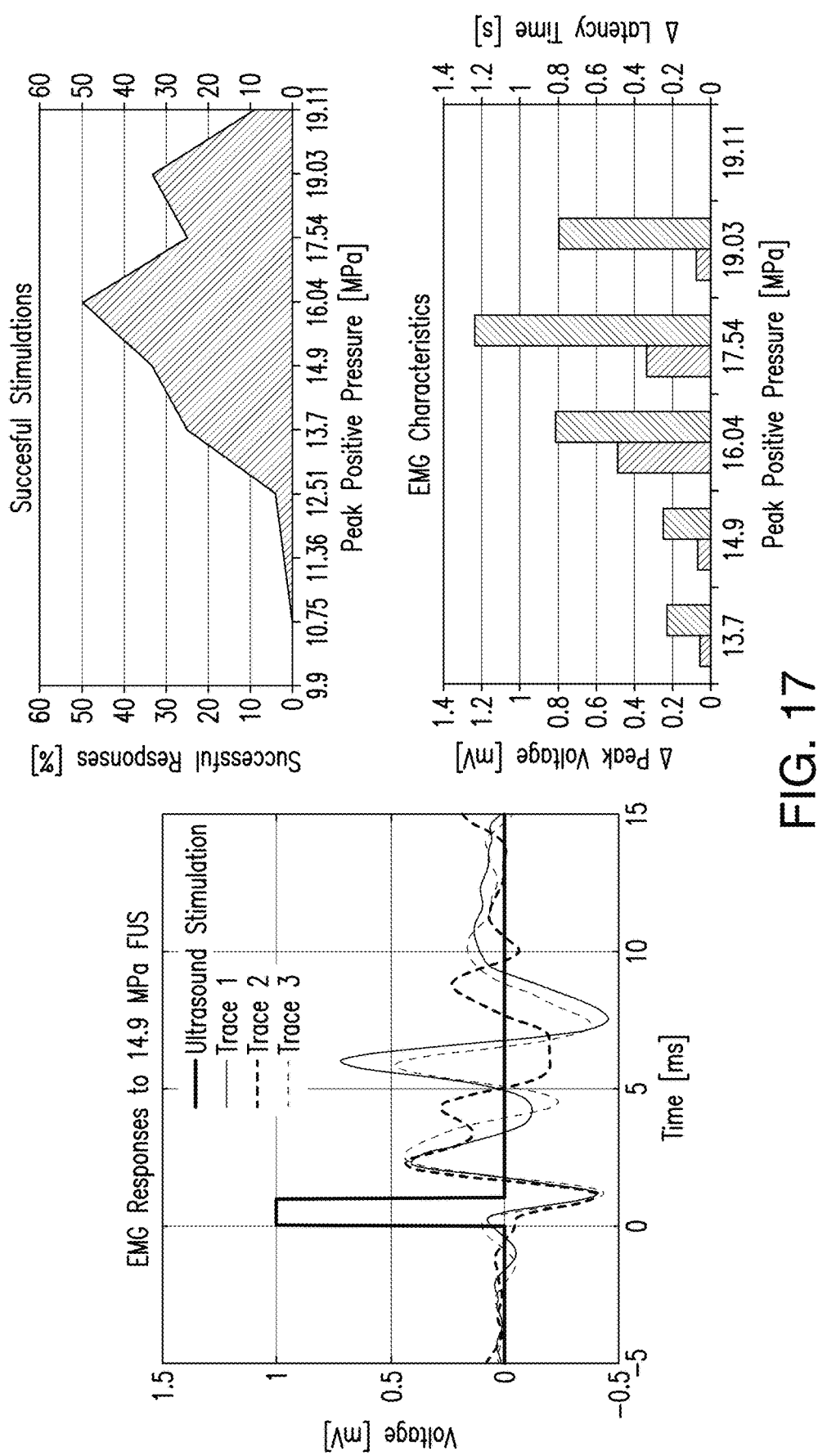
FIG. 17 is a graph showing characterization of EMG responses.
Figure 18:
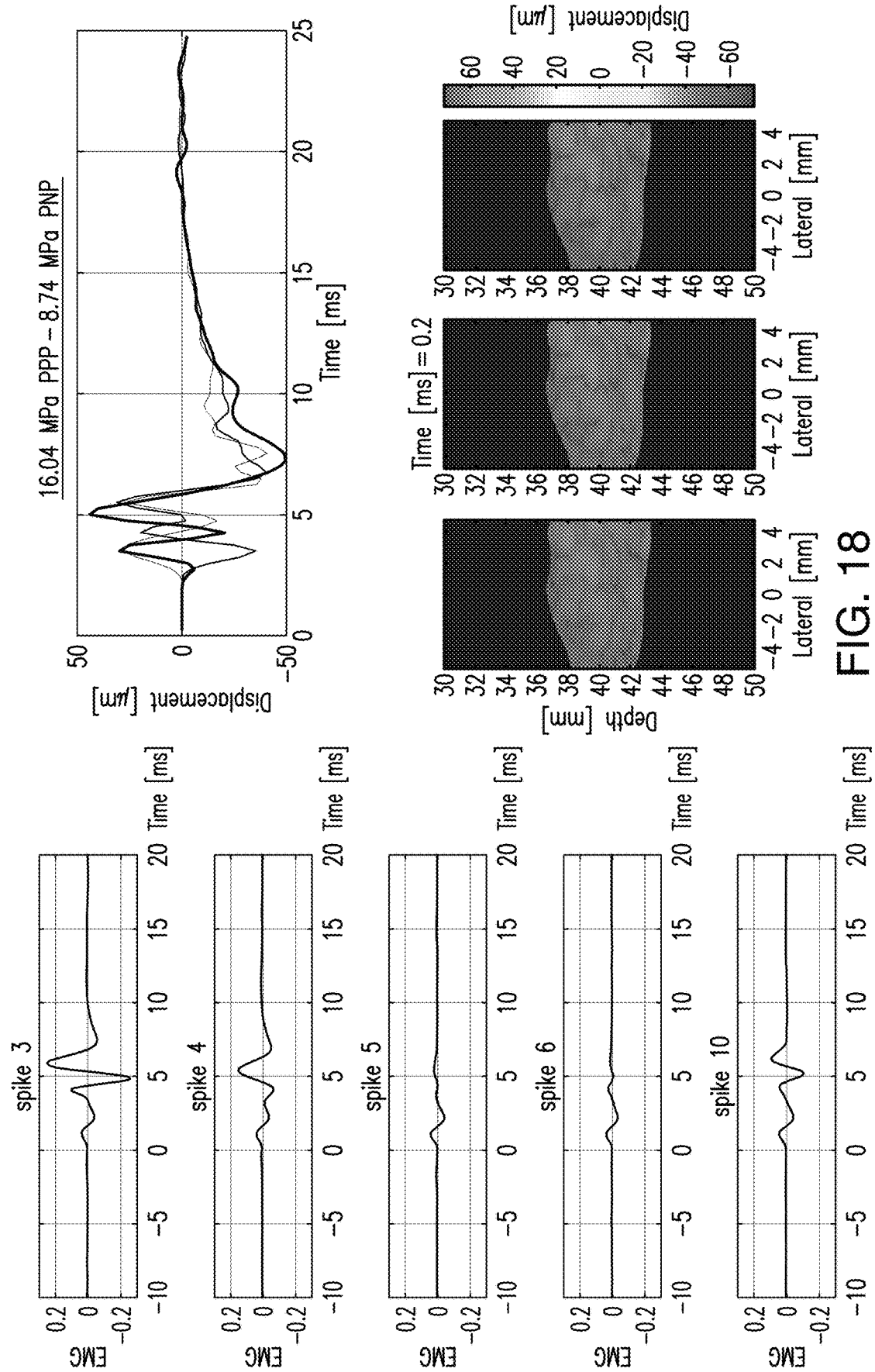
FIG. 18 is a graph showing varied EMG responses and tissue displacements at pressures higher than 16 MPa peak positive pressure (PPP), 8.74 MPa peak negative pressure (PNP).

FIG. 16A is a graph showing displacement imaging modulation with increasing pressures. FIG. 16B is a graph showing individual frames of displacement imaging with 9 MPa pressure. The data demonstrate that more tissue is affected with increasing pressures and therefore indicate that more of the nerve is influenced. EMG response characterization reveals max variation in latency and that peak to peak response occurs around 700-750 mV. Successful responses also maximize returns at these pressure/intensity levels. FIG. 17 is a graph showing characterization of EMG responses. FIG. 18 is a graph showing varied EMG responses and tissue displacements at pressures higher than 16 MPa peak positive pressure (PPP), 8.74 MPa peak negative pressure (PNP). It demonstrates that at high pressures, area of tissue affected by FUS stimulation becomes varied, which may correlate with more varied EMG responses.

Figure 19A:
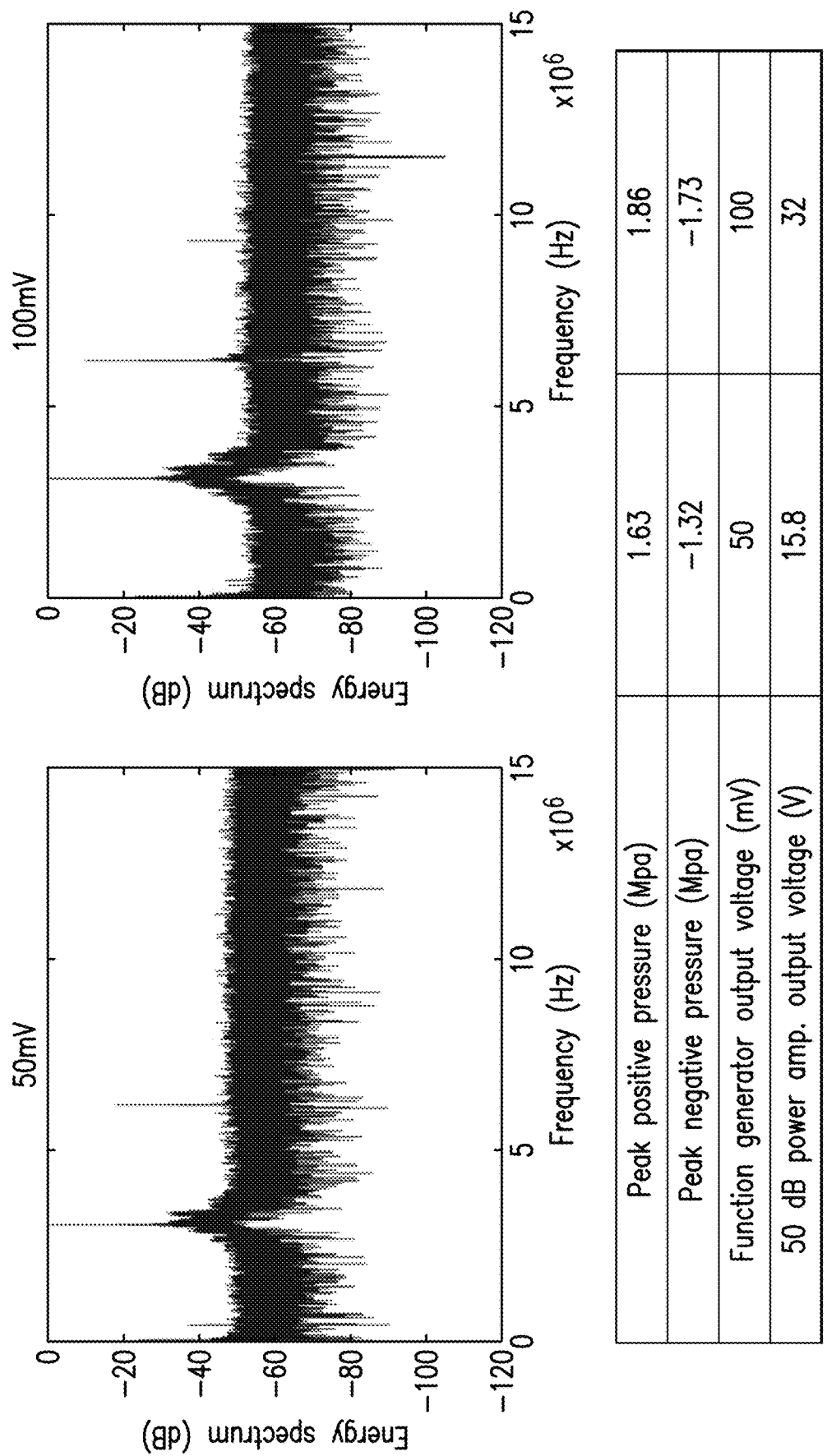
FIGS. 19A-19D are graphs showing induction of stable and inertial cavitations with different pressures.
Figure 19B:
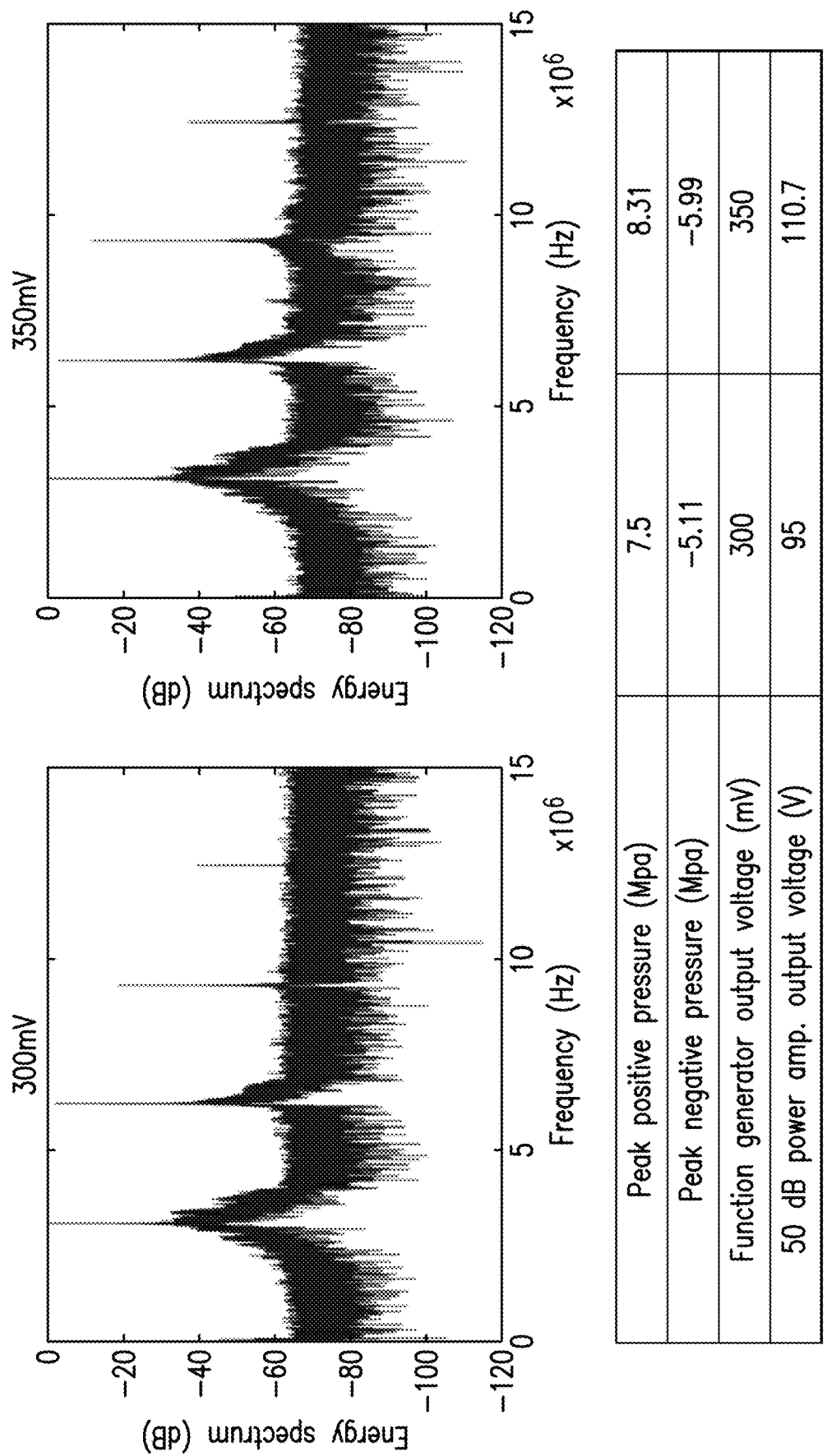
Figure 19C:
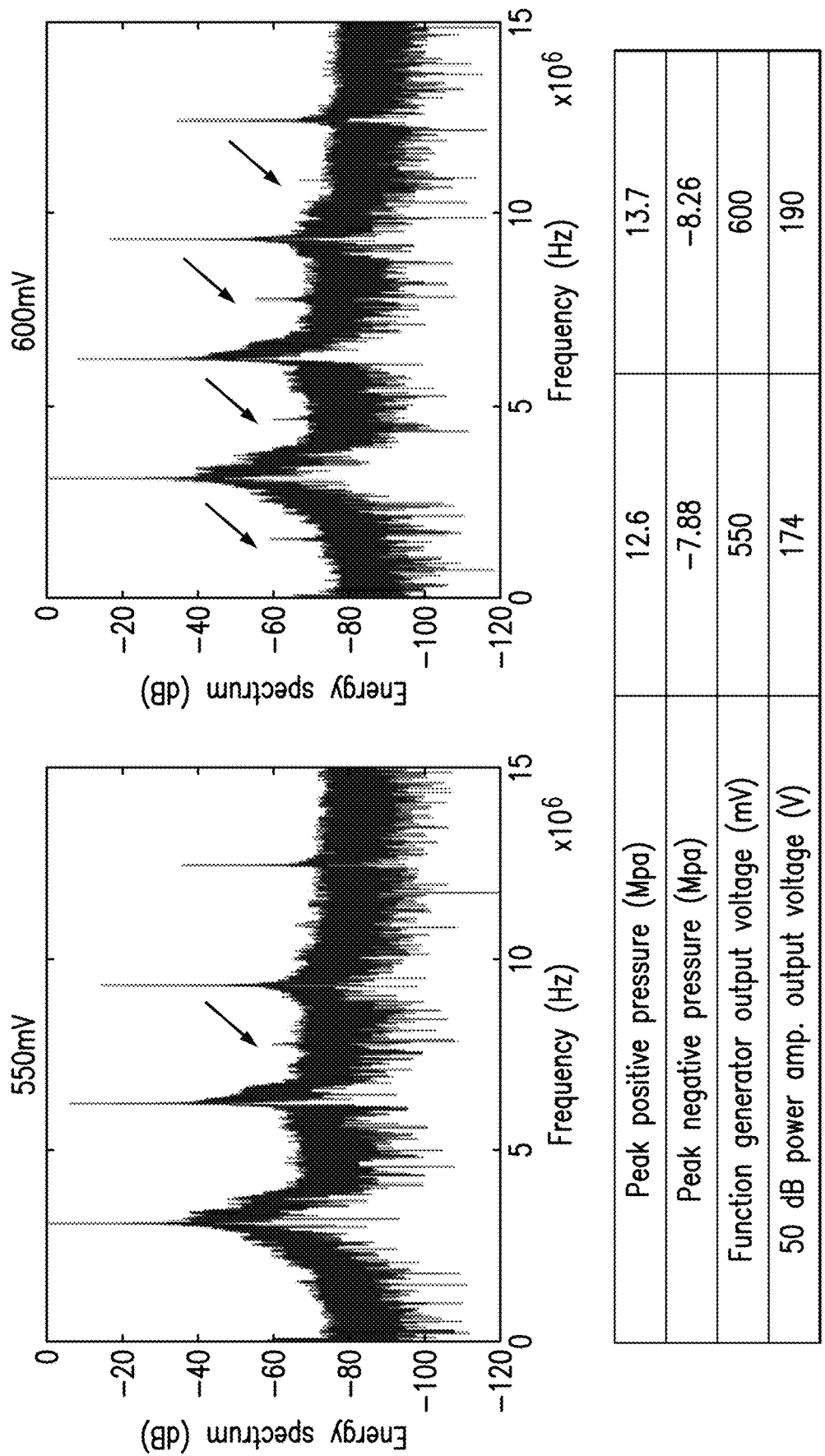
Figure 19D:
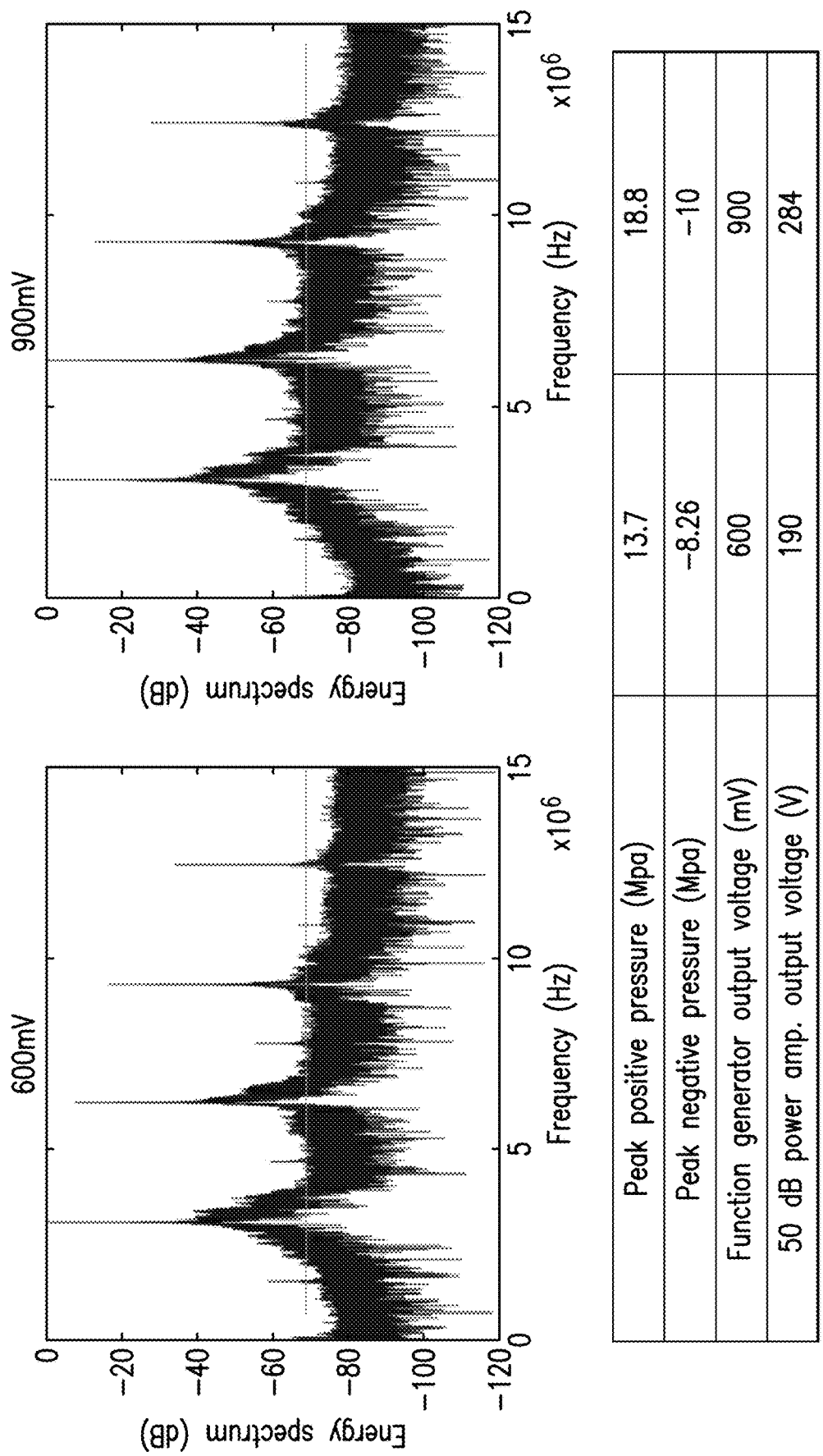

FIGS. 19A-19D are graphs showing induction of stable cavitation and inertial cavitation with different pressures. FIG. 19A is a graph showing no ultraharmonics or broadband emissions. FIGS. 19B and 19C are graphs showing ultraharmonics without broadband emissions. FIG. 19D is a graph showing ultraharmonics and broadband emissions. These data provide evidence that stable cavitation is induced at lower pressures and inertial cavitation is induced at higher pressures. This also corresponds to more consistent EMG responses at stable cavitation ranges, fewer responses at inertial cavitation ranges, and no response below stable cavitation ranges. Ongoing studies will further investigate the link between the nerve displacement amplitude and induced muscle activity in vivo.

Example 3: Acute Testing of Non-Invasive Ultrasound Guided and Mediated Peripheral Nerve Modulation in Healthy Volunteers This Example provides methods and systems for non-invasive ultrasound guided and mediated peripheral nerve modulation in healthy individuals. In particular, an example protocol is provided for performing peripheral nerve modulation in human and animal subjects.
Purpose/Policy The purpose of this Example is to provide detailed, step-by-step instructions on the operation of ultrasound-guided and mediated peripheral neuromodulation in healthy volunteers.
Scope This Example applies to the researchers involved in this protocol regarding the use of a custom medical device. Adherence to this Example and its requirements will help mitigate the risk of unexpected outcomes resulting from machine misuse.

Definitions/Acronyms

Transducer: A device that converts electrical signals into mechanical pressures and vice versa Sonication: The time during which acoustic energy is transmitted through the transducer FUS: Focused Ultrasound
UMN: Ultrasound Mediated Neuromodulation
EMG: Electromyography
PNS: Peripheral Nervous System Responsibilities The UMN application should comply with the procedure described herein. It is the responsibility of every researcher listed in this Example to maintain documented evidence of the ultrasound parameters and patient scans in order to validate the effect of ultrasound operated under explicitly specified limits.

Procedures

Description of Focused Ultrasound

The term focused ultrasound describes the distribution of the energy that is concentrated instead of being spread. To achieve a focused energy deposition, a single element, spherical-segment FUS transducer (H-108, Sonic Concepts, Bothell, Wash.) operating at 3.1 MHz (radius: 30 mm; geometric focus length 50 mm; focal length 3 mm; focal width: 0.45 mm) is used, and the FUS transducer is driven using a function generator (Agilent, Palo Alto, Calif., USA) through a 50-dB power amplifier (E&I, Rochester, N.Y., USA). A 5 MHz, phased-array imaging transducer (IP-105, Sonic Concepts, WA, USA; focal depth: 65 mm; 96-element) will be confocally mounted at the central opening of the FUS transducer to achieve overlap of the two foci. The signals received by the imaging probe will be processed using a 128-element vantage machine (Verasonics, Kirkland, Wash., USA) to display B-mode images of the area of stimulation before, during, and after application of therapy in real time.

Description of the Imaging & Positioning Systems

The imaging system consists of a computer and a transducer interface box. The imaging transducer is plugged into the transducer interface box for recording of both B-mode and displacement maps used for targeting of the therapeutic transducer. This computer will also control the stimulation program and all real-time information (B-mode, displacement maps) will be displayed on the monitor.

The positioning system consists of a robotic arm (Kinova Robotics, Quebec, Canada) along with a joystick to control the initial positioning of the transducers. After initial positioning, a program on the Verasonics computer will be used to control the fine motions of the robot arm for the raster scan along with the final positioning of the transducers before stimulation.

Procedure

Before Stimulation

The procedure to the subject and respond to any questions and concerns are described. Once the subject signs the consent form, the process can begin with the planning of the procedure (i.e. excitation and which nerve to target during the procedure).

The Day of Stimulation

The morning of the procedure, 500 ml of water is degassed for a duration of four hours, or until the dissolved O2 content is below 10%. Additionally, ultrasound gel will be degassed for four hours in a centrifuge. Degassed water and gel are necessary as any air will distort the ultrasound beams resulting in lower doses of stimulation, as well as reducing the resolution of B-mode and displacement images.

Once the system is ready, the subject enters the room and sits on the subject table. They are given a questionnaire to fill out, inquiring muscle activation ability and pain in the area of the nerve to be targeted by the therapy. The area where the ultrasound will be applied needs to be shaved as hair will distort the acoustic waves. After shaving the area will be cleaned with water, and then the degassed ultrasound gel will be applied to the area. The transducers are then moved to the target area using the joystick to control the robotic arm. Once the transducers are approximately placed in the targeted area, the software is started. The researcher will then start the B-mode acquisition and use it to align the FUS transducer foci with the region of interest. The B-mode display will show a 2-D image of the region that the therapeutic ultrasound is targeting. Crosshairs on the B-mode image display should align with the selected peripheral nerve. To validate targeting, displacement testing will be conducted. This utilizes the FUS ultrasound at a power output significantly lower than the therapeutic values. The output causes some tissue motion in the focal area, and will be used to confirm the focal area of the therapeutic transducer is on the selected nerve.

At this time, EMG leads will be placed on the skin adjacent to the muscles innervated by the targeted nerve, with the ground placed on another limb away from the region of interest. Once the leads are placed, the EMG software is turned on and parameters are selected to record any EMG activity in the local area of the treatment. Then parameters for modulation will be selected on the software (pressure, duration, duty cycle, pulse repetition frequency) as determined for the individual subject. These selections cannot be greater than the determined safety thresholds and the software will not allow the researcher to select values outside of that range. Once parameters are selected and verified, the researcher will then start the ultrasound software to apply the therapeutic ultrasound to the subject. Targeting and modification of parameters will be repeated as necessary for each individual's therapy treatment. Following the session, the transducers and EMG leads will be removed from the subject and the subject will be given an exit questionnaire regarding the sensations at the target area after the procedure. Follow up questionnaires will be sent to the subject the day after and a week after the procedure.

The Procedure Step-by-Step (for the Researchers)

For this procedure, up to two researchers may be used (Researcher #1; Researcher #2).

Before Subject Arrival

1) Degas 500 ml of water for 4 hours or until the 02% levels are less than 10% when read from a dissolved oxygen meter (researcher 1)
2) Degas ultrasound gel in a centrifuge at 900 RPM for 4 hours (researcher 1)

Following Subject Arrival

1) Provide the entrance questionnaire to the subject (researcher 2)
2) Power on all equipment (researcher 1)
   a. Verasonics computer
   b. Verasonics transducer tower
   c. Function generator
   d. Amplifier
   e. Matching Box
   f. Robotic Arm
   g. Biopac EMG recording hardware
3) Fill water bladder from the top of the H-108 transducer full and place the imaging probe in the center aperture (researcher 1)
4) Bring in the subject and situate them comfortably on the procedure table (researcher 2)
5) Remove hair by shaving (5 cm diameter) the target limb region on the subject (researcher 2)
6) Apply degassed ultrasound gel to the newly shaved target area (researcher 2)

7) Place EMG leads on skin adjacent to the FUS stimulation (researcher 2)
   a. One EMG lead per each side of the transducer and place the ground on another limb
   b. Start the recording software to assess stability and quality of recordings
8) Position the ultrasound transducer system on the target region using the robotic arm joystick (researcher 1)
9) Start the imaging/Stimulation program on the Verasonics computer (researcher 1)
10) Using the real-time B-mode image, locate the target nerve (researcher 2)
11) Probe the region of interest using the displacement function to verify the focal area of the stimulation transducer is indeed on the nerve (researcher 2)
12) Select initial pressure, duration, and duty cycle for therapeutic ultrasound dose (researcher 2)
13) If the subject indicated willingness for video recordings, position the webcam where no individual markings or ways to identify the subject are in the viewfinder and start video recordings (researcher 1)

Treatment
1) Click "start treatment" to start the therapy (researcher 2)
2) Increase acoustic power until safety limit is reached or the subject indicates any response to the treatment (researcher 2)
3) Every minute, assess the state of the subject for any signals to stop the procedure (researcher 2)

Post-Treatment
1) Store all EMG data, displacement maps, B-mode images, and video recordings into the encrypted computer (researcher 1)
2) Remove the ultrasound system from the subject using the robotic arm joystick (researcher 2)
3) Clean ultrasound gel from the subject's skin (researcher 2)
4) Remove all EMG leads from the subject's skin (researcher 2)
5) Provide the subject with the exit questionnaire (researcher 2)

The contents of all figures and all references, patents and published patent applications and Accession numbers cited throughout this application are expressly incorporated herein by reference.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

What is claimed is:

1. A method for modulation of a peripheral nerve in a subject using a focused ultrasound (FUS) assembly having one or more ultrasound parameters, comprising:
   adjusting the one or more ultrasound parameters to adapt a FUS for a location on the peripheral nerve, wherein the one or more ultrasound parameters are adjusted to induce a displacement of the peripheral nerve ranging from about 8.5 µm to about 422 µm and elicit an electromyography (EMG) activity at the peripheral nerve without damaging or ablating the peripheral nerve;
   modulating the peripheral nerve using the FUS with the adjusted one or more ultrasound parameters; and
   imaging the modulated peripheral nerve resulting from the FUS.

2. The method of claim 1, further comprising locating the peripheral nerve using an imaging probe prior to adjusting the one or more ultrasound parameters.

3. The method of claim 2, wherein the imaging probe comprises a B-mode imaging probe.

4. The method of claim 1, wherein the peripheral nerve comprises a sciatic nerve, a tibial nerve, or a sacral nerve.

5. The method of claim 1, wherein the FUS assembly comprises a high intensity focused ultrasound (HIFU) transducer with a 3.57 MHz center frequency, a 0.46×3.55 mm focal area and a 35 mm focal depth, a 20 MHz function waveform generator, and a 150 W amplifier.

6. The method of claim 1, wherein the one or more ultrasound parameters comprise at least one of a peak negative pressure, a stimulation duration, a duty cycle, and a pulse repetition frequency (PRF).

7. The method of claim 6, wherein the peak negative pressure is from about 1.1 MPa to about 8.8 MPa.

8. The method of claim 6, wherein the stimulation duration is from about 0.8 ms to about 1 s.

9. The method of claim 6, wherein the duty cycle is from about 15% to about 100%.

10. The method of claim 6, wherein the PRF is from about 1 kHz to about 50 kHz.

11. The method of claim 6, wherein the peak negative pressure is from about 3.2 MPa to about 5.7 MPa, the stimulation duration is from about 0.8 ms to about 10.5 ms, the duty cycle is from about 35% to about 100%, and the PRF is from about 1 kHz to about 50 kHz.

12. The method of claim 1, further comprising eliciting and measuring a physiological response during or after FUS modulation.

13. The method of claim 12, wherein measuring the physiological response comprises acquiring electromyography (EMG) signals from a muscle tissue.

14. The method of claim 12, further comprising modulating the one or more ultrasound parameters to change timing of the physiological response.

15. The method of claim 1, further comprising monitoring a thermal effect elicited by the FUS modulation.

16. A system for modulating a peripheral nerve in a subject using focused ultrasound (FUS), comprising:
   an imaging probe for locating the peripheral nerve;
   an ultrasound assembly, including a high intensity focused ultrasound (HIFU) transducer, a function generator, and an amplifier, for providing a FUS having one or more ultrasound parameters to a location on the peripheral nerve, wherein the ultrasound assembly is configured to adjust one or more ultrasound parameters to induce a displacement of the peripheral nerve ranging from about 8.5 µm to about 422 µm and elicit an electromyography (EMG) activity at the peripheral nerve without damaging the peripheral nerve, wherein the ultrasound assembly comprises a transdermal patch; and a processor, coupled to the ultrasound assembly, for adjusting the one or more ultrasound parameters to adapt the FUS for a location on the peripheral nerve.

17. The system of claim 16, wherein the HIFU comprises a transducer with a 3.57 MHz center frequency, a 0.46×3.55 mm focal area and a 35 mm focal depth.

18. The system of claim 16, wherein the function generator comprises a 20 MHz function waveform generator, and the amplifier comprises a 150 W amplifier.

19. The system of claim 16, further comprising a mechanical positioning system for placing the ultrasound assembly and the imaging probe.

20. The system of claim 16, further comprising an imaging system, operatively coupled to the processor and the imaging probe, for recording and displaying the peripheral nerve and/or surrounding tissue during FUS modulation.

21. The system of claim 20, wherein the imaging probe comprises a pulse-echo image transducer.

* * * * *

UNITED STATES PATENT AND TRADEMARK OFFICE
CERTIFICATE OF CORRECTION

PATENT NO. : 11,013,938 B2
APPLICATION NO. : 15/661909
DATED : May 25, 2021
INVENTOR(S) : Elisa E. Konofagou and Matthew Downs Page 1 of 1

It is certified that error appears in the above-identified patent and that said Letters Patent is hereby corrected as shown below:

In the Specification

In Column 1, Lines 19-23, under the heading, STATEMENT REGARDING FEDERALLY-SPONSORED RESEARCH please correct:
"This invention was made with government support under grants EB009041 and AG038961 awarded by the National Institutes of Health and by HR0011-15-2-0054 awarded by DOD/DARPA. The government has certain rights in the invention."

To read:
-- This invention was made with government support under HR0011-15-2-0054 awarded by the Defense Advanced Research Projects Agency, and EB009041, and AG038961 awarded by the National Institutes of Health. The government has certain rights in the invention. --

Signed and Sealed this
Fourth Day of July, 2023

Katherine Kelly Vidal
*Director of the United States Patent and Trademark Office*